United States Patent
Dohm et al.

(10) Patent No.: US 8,759,646 B2
(45) Date of Patent: *Jun. 24, 2014

(54) OSTEOSPERMUM AND DIMORPHOTECA PLANTS HAVING AN ALTERED FLOWER PHENOTYPE

(75) Inventors: Andrea Dohm, Pforzheim (DE); Ulrich Sander, Stuttgart (DE); Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 442 days.

This patent is subject to a terminal disclaimer.

(21) Appl. No.: 13/077,351

(22) Filed: Mar. 31, 2011

(65) Prior Publication Data

US 2011/0247105 A1 Oct. 6, 2011

Related U.S. Application Data

(63) Continuation-in-part of application No. 12/750,965, filed on Mar. 31, 2010.

(30) Foreign Application Priority Data

Mar. 31, 2010 (EP) ..................................... 10158786

(51) Int. Cl.
*A01H 4/00* (2006.01)
*A01H 5/00* (2006.01)
*A01H 5/10* (2006.01)

(52) U.S. Cl.
USPC ............................. 800/323; 435/410; 800/298

(58) Field of Classification Search
None
See application file for complete search history.

(56) References Cited

U.S. PATENT DOCUMENTS

| | | | |
|---|---|---|---|
| 5,684,225 A | 11/1997 | Drewlow et al. | |
| PP10,342 P | 4/1998 | Sorensen | |
| 6,150,591 A | 11/2000 | Hanes et al. | |
| PP12,020 P2 | 7/2001 | Rother | |
| PP12,149 P2 | 10/2001 | Rother | |
| PP15,828 P2 * | 7/2005 | Kawashima | |
| PP15,866 P2 * | 7/2005 | Kawashima | |
| PP16,564 P3 | 5/2006 | Larsen | |
| PP17,419 P2 | 2/2007 | Larsen | |
| PP17,703 P3 | 5/2007 | Larsen | |
| PP18,330 P3 | 12/2007 | Kaagman | |
| PP23,304 P2 * | 1/2013 | Klemm et al. | |
| PP23,388 P3 * | 2/2013 | Klemm et al. | |
| 2011/0247092 A1 * | 10/2011 | Dohm et al. .................. | 800/260 |
| 2011/0247095 A1 | 10/2011 | Dohm et al. | |

FOREIGN PATENT DOCUMENTS

EP 10158786 5/2010
EP 11160693.5 10/2011

OTHER PUBLICATIONS

Krause et al 2003, Journal of Frit and Ornamental Plant Research 11: 107-112.*
Al-Atabee et al 1987, Plant Cell Reports 6: 414-416.*

(Continued)

*Primary Examiner* — David H Kruse
(74) *Attorney, Agent, or Firm* — James M. Weatherly; Cochran Freund & Young LLC

(57) ABSTRACT

The instant invention relates to an altered flower shape in plants belonging to the genera *Osteospermum* and *Dimorphoteca*, which is induced by a mutant allele, as well as to the method of breeding *Osteospermum* and *Dimorphoteca* plants having this altered flower shape.

16 Claims, 15 Drawing Sheets

(56) References Cited

OTHER PUBLICATIONS

Christie, B.R. and Choo, T.M., Effects of harvest time and Alar-85 on seed yield of red clover, Canadian Journal of Plant Science, vol. 70, No. 3, 1990, pp. 869-871.

DeJong, J., et al., "Genetic Analysis in *Chrysanthemum morifolium*. II. Flower Doubleness and Ray Floret Corolla Splitting," Euphytica 33: 465-470 (1984).

Drennan, D., et al., "Heritability of Inflorescence and Floret Traits in *Gerbera*," Euphytica 35: 319-330 (1986).

Börstling, D., "Transformation von Zierpflanzen: Methoden und Anwendungen," Technische Universität München, Jun. 13, 2001.

Allavena, A., et al., "Genetic Engineering of *Osteospermum* SPP: A Case Story," ISHS ACTA Horticulturae 508: XIX International Symposium on Improvement of Ornamental Plants, 508: 129-133 (2000).

Al-Atabee, J. S., et al., "Plant Regeneration from Protoplasts of *Dimorphotheca* and *Rudbeckia*," Plant Cell Reports, 6(6): 414-416 (1987).

Rabaglio, M., et al., "Manipolazione In Vitro Della Dimorfoteca (*Osteospermum* SPP.)," !Italus Hortus, 2(3): 56-59 (Jun. 1995).

CPVR Grant 15701, EU, Jun. 6, 2005, Sunny Gronnegyden Aps.

CPVR Grant 34096, EU, Jul. 8, 2011, Nils Klemm.

Response filed on Jul. 11, 2013 in European Patent Application 11160693.5.

Faccioli et al. Plant Breeding, 2000; 119:351-355, 351.

Allavena et al. Acta Hort, 508, 129-133, ISHS 2000.

Berio et al., Acta Hort. 546, 171-176, ISHS 2001.

Official Gazette of the Community Plant Breeder's Rights 200301237 Publication Notice for Application No. CPVR 15701, "Sunny Elizabeth", Aug. 15, 2005, Sunny Grønnegyden ApS, p. 61.

U.S. Appl. No. 12/750,965, Dohm, et al.

* cited by examiner a)

b)

c)

OSTEOSPERMUM AND DIMORPHOTECA PLANTS HAVING AN ALTERED FLOWER PHENOTYPE

CROSS REFERENCE RELATED TO APPLICATION

This application is a continuation-in-part of and claims priority under 35 U.S.C. §120 from U.S. application Ser. No. 12/750,965, which was filed Mar. 31, 2010, and from European Patent Application No. 10158786.3, which was filed Mar. 31, 2010, both of which are incorporated by reference herein in their entirety.

INCORPORATION OF SEQUENCE LISTING

A copy of the sequence listing in a computer-readable form and named 1574-067CIP.txt, which is approximately 5.0 kilo bases and was created on Mar. 31, 2011, is filed herewith via the USPTO EFS system and is hereby incorporated by reference.

BACKGROUND OF THE INVENTION

The instant invention relates to an altered flower shape in plants belonging to the genera *Osteospermum* and *Dimorphoteca*, which is induced by a mutant allele, as well as to the method of breeding *Osteospermum* and *Dimorphoteca* plants having this altered flower shape.

The genus *Osteospermum* was introduced as a commercial bedding plant in the beginning of the nineties of the last century. Since then this genus has been very successful in the horticultural market. For 2008, worldwide sales were estimated at almost 100 million plants.

The genus *Osteospermum* is a South African native and belongs to the plant family of the Asteraceae. It comprises almost 70 different species representing a broad range of either evergreen shrubs or herbaceous plants with growing habits varying from erect to prostrate. The existing *Osteospermum* cultivars are thought to be interspecific hybrids of the following main species: *O. ecklonis, O. barbariae, O. caulescens, O. fruticosum, O. jucundum,* and *O. chrysanthemifolia*. The first breeding with *Osteospermum* was started between 1970 and 1985 by British hobby breeders and later continued mainly by Danish and Japanese breeders (Allavena, A., et al., Genetic engineering of *Osteospermum* ssp.: a case story, *Acta Hort.*, 508, 129-133 (2000)). According to Faccioli, et al., professional breeders used the British plant material as well as accessions from South Africa to breed new hybrids (Faccioli, P., et al., Genetic diversity in cultivated *Osteospermum* as revealed by random amplified polymorphic DNA analysis, *Plant Breed.*, 119, 351-355 (2000)). During further breeding, which was mainly done by professional Danish and German breeding companies, crossings between the existing plants were made to improve the quality. This approach has resulted in a narrow gene pool of the plant material which is commercially available today. The genera *Osteospermum* and *Dimorphoteca* are very closely related and, in some cases, even the distinction of both genera or the classification of certain varieties into these two genera is unclear. In the past the genus *Osteospermum* belonged to the genus *Dimorphoteca*, but today *Dimorphoteca* only comprises the annual species, whereas all semi-perennial species fall into the genus *Osteospermum*. Crossbreeding between both genera is possible and several commercial varieties result from intergeneric hybridization between an *Osteospermum* and a *Dimorphoteca* parent. The different *Osteospermum* and *Dimorphoteca* cultivars, breeding lines and wild species represent a broad range of different ploidy levels varying from 2× up to almost 8×, which also shows that during the development of today's cultivars hybridization between species took place. For commercial production, *Osteospermum* and *Dimorphoteca* plants are mostly propagated asexually by cuttings. However, sexual propagation through seeds is also possible and several seed propagated varieties are on the market.

Commercially available *Osteospermum* plants flower from early spring to autumn. The typical flower is a capitulum (flower head) with tubular central disc florets surrounded by a ring of ray florets, which gives the flowers the typical daisy shape (Faccioli, P., et al., Genetic diversity in cultivated *Osteospermum* as revealed by random amplified polymorphic DNA analysis, *Plant Breed.*, 119: 351-355 (2000)). The color and shape of ray florets as well as the color of the disc florets vary. The color of the upper surface of the ray florets, which in colloquial language are called petals, is determined by two independent metabolic pathways producing carotenoids, visible as yellow-orange-brown colors, and anthocyanins, resulting in white to pink and purple flower colors (Seitz, C., Klonierung and Charakterisierung von Flavonoidgenen aus *Osteospermum*, Dissertation an der Technischen Universität München (2004)). Intensive breeding work during the past several years has resulted in a broad range of white, pink, purple, yellow, and orange petal colors and new mixes of the carotenoid and anthocyanin color groups, as well as in color patterns like eye types or stripes. Similar to the color range of the upper surface, the color of the lower surface of the ray florets also varies from light to dark colors in the bluish-pink or yellow-brown color range. The color pattern usually is striped with the colored stripes running parallel to the petal edges. Typically, the color of the disc florets is darker than the color of the ray florets and it may vary from grey to blue, violet or purple or from dark yellow to dark brown. The usual shape of the ray floret is obovate, but in some genotypes the petal edges are rolled upwards resulting in so-called spoon or spider types.

An *Osteospermum* and *Dimorphoteca* breeding program was established in 2002 to produce altered flowering *Osteospermum* and *Dimorphoteca* plants. *Osteospermum* plants with unusual inflorescences are desirable, as altered flowers, which display mainly enlarged disc florets, are believed to stay open even in complete darkness, whereas normal flowers close under low light conditions (less than 2000 Lux).

Furthermore, for the altered flowering plants, the keepability of the flowers is longer both in the field and in the greenhouse compared to the flowers on a normal-flowering plant. This extended flower keepability is believed to result from a reduced seed set due to the limited pollen availability on the altered flowering plants. This limited pollen availability is a direct consequence of the enlarged disc florets which prevent the pollinating insects from reaching the pollen.

Finally, although most commercially available *Osteospermum* and *Dimorphoteca* varieties or assortments are vegetatively propagated by cuttings, several varieties or assortments of the genera *Osteospermum* and *Dimorphoteca* such as "Asti" and "Passion Mix" are propagated by seeds. For the production of $F_1$ hybrids of the seed-propagated varieties, the flowers of the female crossing parent usually have to be emasculated to prevent self-pollination and then are pollinated with pollen of a selected male parent to produce hybrid seeds. To avoid the labor intensive and costly emasculation and hand pollination procedures, a system that inhibits self pollination on the bisexual *Osteospermum* and *Dimorphoteca* plants would be highly desirable. In some plant species biological systems like male sterility or self incompatibility can be used in this respect, but these systems are not described for *Osteospermum* or *Dimorphoteca*. However, in case of *Osteospermum* and *Dimorphoteca* plants, which exhibit the altered flower type with enlarged disc florets, anthers are covered by the enlarged disc florets and hence the pollen is not freely available for pollinating insects. Therefore, hybrid seeds from these plants can be obtained without emasculation by insect pollination, which reduces the costs for $F_1$ hybrid seed production significantly.

For the above reasons, it is desirable to develop altered flowering *Osteospermum* and *Dimorphoteca* plants which show enlarged disc florets.

Several approaches such as mutation treatment and interspecific and intergeneric crosses were attempted to achieve an altered flowering trait in the genera *Osteospermum* and *Dimorphoteca*.

Several experiments on induction of mutations by Gamma-irradiation of *Osteospermum* and *Dimorphoteca* plant material were performed. Examples of references that illustrate alteration of flower type via mutation are altered flower type in ornamental sweet potato (Bhate, R. H., Chemically Induced Floral Morphological Mutations in Two Cultivars of *Ipomoea purpurea* (L.) Roth, *Scientia Horticulturae* 88: 133-145 (2001)); in Chrysanthemum (Rana, R. S., Radiation-Induced Variation in Ray-Floret Characteristics of *Annual Chrysanthemum*, *Euphytica*. 8: 270-322 (1965)); in roses (Teruo, N., Ikegami, Y., Matsuda, Y., and Toyoda, H., Induction of Morphologically Changed Petals from Mutagen-Treated Apical Buds of Rose and Plant Regeneration from Varied Petal-Derived Calli, *Plant Biotechnology*, 8: 233-236 (2001)); and in plants in general (Krasaechai, A. L. D., et al., Low-Energy Ion Beam Modification of Horticultural Plants for Induction of Mutation, *Surface and Coatings Technology*, 203: 2525-2530 (2009)). In this regard it is important to mention that the ploidy level of almost all *Osteospermum* cultivars is tetraploid, whereas the ploidy level of *Dimorphoteca* cultivars varies from 2× to 6×. This means that in the case of a recessive mutation at least two generations would be necessary for the phenotype of any recessive mutation to become visible. In the case of a dominant mutation the phenotype would become visible in the M0-generation.

A first set of experiments was performed by the applicant on mature seeds which had been harvested from different *Dimorphoteca* cultivars. Batches of 30 seeds each were treated with doses of Gamma-irradiation varying from 15 to 40 Gy for periods varying from 5 to 30 minutes. Immediately after this treatment the seeds were soaked in a solution of 10% Polyethylene glycol (PEG) for 4 hours, the solution was washed off and the seeds were sown in standard seedling substrate. Germination started after about one week. Three weeks after sowing, when the first pair of leaves had developed, the seedlings were transplanted. Three weeks after transplanting, the seedlings were planted into 11 cm diameter pots and grown according to standard protocols. First flowering started about 10 weeks after potting. The plant populations were continuously evaluated for effects or mutants caused by the Gamma-irradiation. Depending on the dosage and the period of irradiation fewer seeds germinated and more malformed seedlings appeared, which did not develop further. Alterations of the growing habit as well as altered foliage types were difficult to evaluate, because the seeds originated from crossbreeding and therefore segregation of these characters in the offspring was expected. However, altered flower colors appeared, which resulted from mutation and not from segregation of the parental flower colors. These new colors showed that overall mutations of flower characteristics had successfully been induced by Gamma-irradiation. However, no altered flower shapes were detected in these plant populations.

A second set of experiments was performed by the applicant on rooted cuttings from different *Dimorphoteca* cultivars. Cuttings were rooted in standard paper pots within a period of 4 weeks. After successful rooting the cuttings were pinched above the 5th leaf pair and immediately Gamma irradiated. The dosages and irradiation periods corresponded to the previous experiments on seeds. After irradiation the cuttings were planted into 11 cm diameter pots containing a standard growing substrate and cultivated under standard growing conditions. The young plants were pinched back twice over a period of 6 weeks in order to allow mutated cells to develop into shoots. Flowering started about 13 weeks after planting. The plants were continuously evaluated for mutants. Several altered growing habits, foliage shapes, and flower colors were detected. However, altered flower shapes did not appear on any of the irradiated plants.

Interspecific and Intergeneric Crosses

Representatives from different species of the genera *Osteospermum* and *Dimorphoteca* were collected and crossing experiments with commercial *Osteospermum* cultivars were performed. In all combinations one parent was a commercial variety.

Occasionally, in *Osteospermum* seedling progeny individual plants were detected which exhibited an additional whorl of ray florets. These florets, which were located at the base of the main ray florets, were significantly narrower than the main ray florets and orientated vertically to the first whorl. These flowers still produced female organs at the base of the ray florets and were female fertile which was proven by their seed set. This additional whorl of ray florets was not stable and showed significant genotype-environment interaction. The respective plants were self-pollinated as well as crossbred to stabilize this phenotype. However, the trait was not detected in any of the progeny and therefore it is obviously not genetically stable. In summary, interspecific or intergeneric seed set was achieved for only two combinations, which was shown by an intermediate phenotype of the offspring. Among this offspring, as well as in further generations produced from these plants, no stable altered flowering plants were detected.

Hence, there is still a need for stable altered flowering plants having enlarged disc florets. The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary, not limiting in scope. In various embodiments, one or more of the above-described problems have been reduced or eliminated, while other embodiments are directed to other improvements.

The present invention relates to an altered flower phenotype in *Osteospermum* and *Dimorphoteca* expressed in the formation of enlarged or converted disc florets. This altered flower type is induced by a mutant allele called the KLEDF allele.

The invention additionally relates to new *Osteospermum* and *Dimorphoteca* plants characterized by their unique flowers which may be produced by the described methods.

Furthermore, the invention relates to pollen, seed, and sexual, as well as asexual progeny of such plants with altered flowers.

In addition, the invention relates to methods for propagating said plants and to uses of said plants.

Further, the invention relates to a method for producing an *Osteospermum* plant having an altered flower phenotype, wherein the method comprises crossing an *Osteospermum* plant of the present invention with a different *Osteospermum* plant not having an altered flower phenotype.

Another embodiment of the present invention provides a method for producing a *Dimorphoteca* plant having an altered flower phenotype, wherein the method comprises crossing the *Dimorphoteca* plant of the present invention with a different *Dimorphoteca* plant not having an altered flower phenotype.

In a further embodiment of the present invention a method for producing an intergeneric hybrid plant having an altered flower phenotype is provided, wherein the method comprises crossing the *Osteospermum* plant of the present invention with the *Dimorphoteca* plant of the present invention.

The invention also relates to a method for producing an intergeneric hybrid plant having an altered flower phenotype, wherein the method comprises crossing the *Osteospermum* plant of the present invention with a *Dimorphoteca* plant not having an altered flower phenotype.

Additionally, the present invention relates to a method for producing an intergeneric hybrid plant having an altered flower phenotype, wherein the method comprises crossing the *Dimorphoteca* plant of the present invention with an *Osteospermum* plant not having an altered flower phenotype.

Furthermore, the present invention relates to a method for producing *Osteospermum* seed comprising crossing a first parent *Osteospermum* plant with a second parent *Osteospermum* plant and harvesting the resultant seed, wherein said first and/or second parent *Osteospermum* plant is the *Osteospermum* plant of the present invention.

Another embodiment of the present invention provides a method for producing intergeneric seed, wherein the method comprises crossing the *Osteospermum* plant of the present invention with a *Dimorphoteca* plant and harvesting the resulting intergeneric seed.

In still another embodiment of the present invention, a method for producing intergeneric seed is provided, wherein the method comprises crossing the *Osteospermum* plant of the present invention with a *Dimorphoteca* plant not having an altered flower phenotype and harvesting the resulting intergeneric seed.

Further, the present invention relates to a method for producing intergeneric seed, wherein the method comprises crossing the *Dimorphoteca* plant of the present invention with an *Osteospermum* plant not having an altered flower phenotype and harvesting the resulting intergeneric seed.

The present invention also refers to the use of the primers according to SEQ ID NOs: 1 and 2 for identifying plants with an altered flowering phenotype. Preferably, the plants are plants of the genus Asteraceae. More preferably, the plants are *Osteospermum* or *Dimorphoteca* plants.

Preferably, the primers are used in an AFLP analysis. Preferably, a fragment of about 151 bp is obtained using these primers.

Further, the present invention refers to the use of the primers according to SEQ ID NOs: 3 and 4 for identifying plants with an altered flowering phenotype. Preferably, the plants are plants of the family Asteraceae. More preferably, the plants are *Osteospermum* or *Dimorphoteca* plants. Preferably, the primers are used in an SNP analysis.

Finally, the present invention relates to a method for transferring the KLEDF mutant allele from one *Osteospermum* plant into another *Osteospermum* or *Dimorphoteca* plant, comprising crossing the *Osteospermum* plant of the present invention with another *Osteospermum* or *Dimorphoteca* plant, collecting $F_1$ seeds from said cross, selfing or crossing the $F_1$ plants derived from said $F_1$ seeds for one or more generations and screening plants derived from said selfing or crossing for the presence of said mutant KLEDF allele.

In addition to the exemplary aspects and embodiments described above, further aspects and embodiments will become apparent by studying the following descriptions.

DEFINITIONS

In the description and tables that follow, a number of terms are used. In order to provide a clear and consistent understanding of the specification and claims, including the scope to be given such terms, the following definitions are provided:

Adapter. Adapter molecules for the AFLP technique are short nucleic acid molecules of which a part is complementary to the sticky end of the restriction fragment and a part is a double strand of known sequence, usually comprising 10 to 15 bp. Exemplary adapter molecules are depicted in SEQ ID NOs: 6 to 9.

Allele. An allele is any of one or more alternative forms of a gene which relate to one trait or characteristic. In a diploid cell or organism, the two alleles of a given gene occupy corresponding loci on a pair of homologous chromosomes.

Figure 2:
FIG. 2 shows a close-up of an altered flowering *Osteospermum* plant with enlarged tubular disc florets enclosing the gynoecium and androecium.
Figure 3:
FIG. 3 shows a close-up of an altered flowering *Osteospermum* plant with enlarged open disc floret transformed into ligulate florets.
Figure 5:
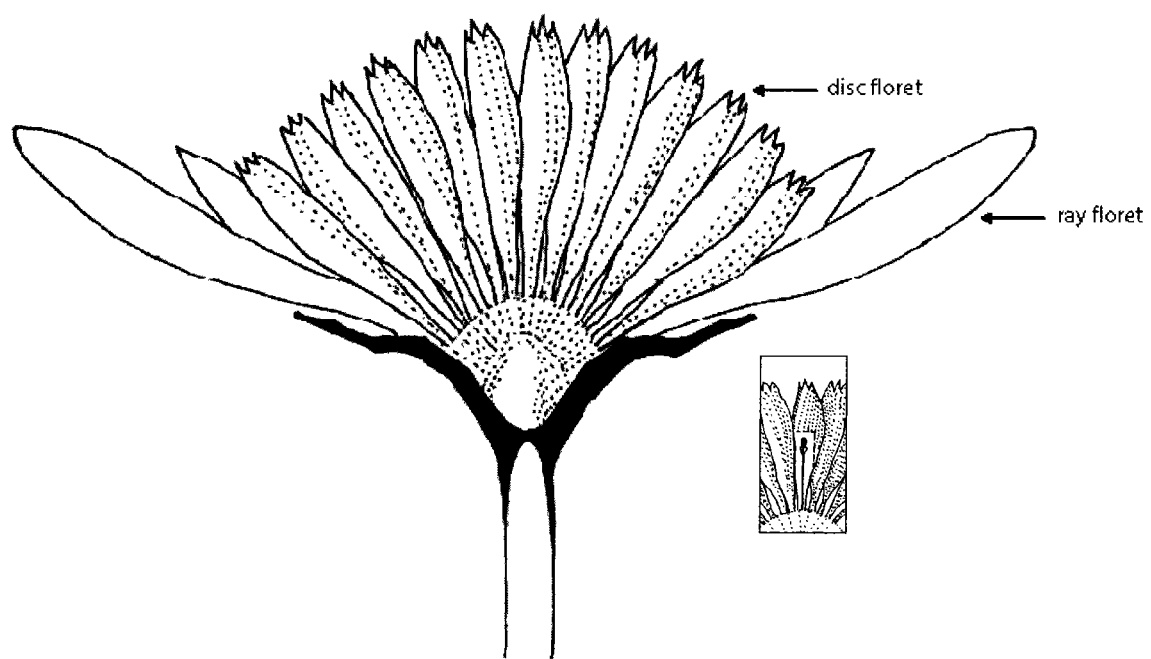
FIG. 5 shows a drawing of a longitudinal cross-section of an inflorescence of an altered flowering *Osteospermum* plant with tubular disc florets. The close-up shows that the enlarged tubular disc floret encloses the gynoecium and androecium.
Figure 6:
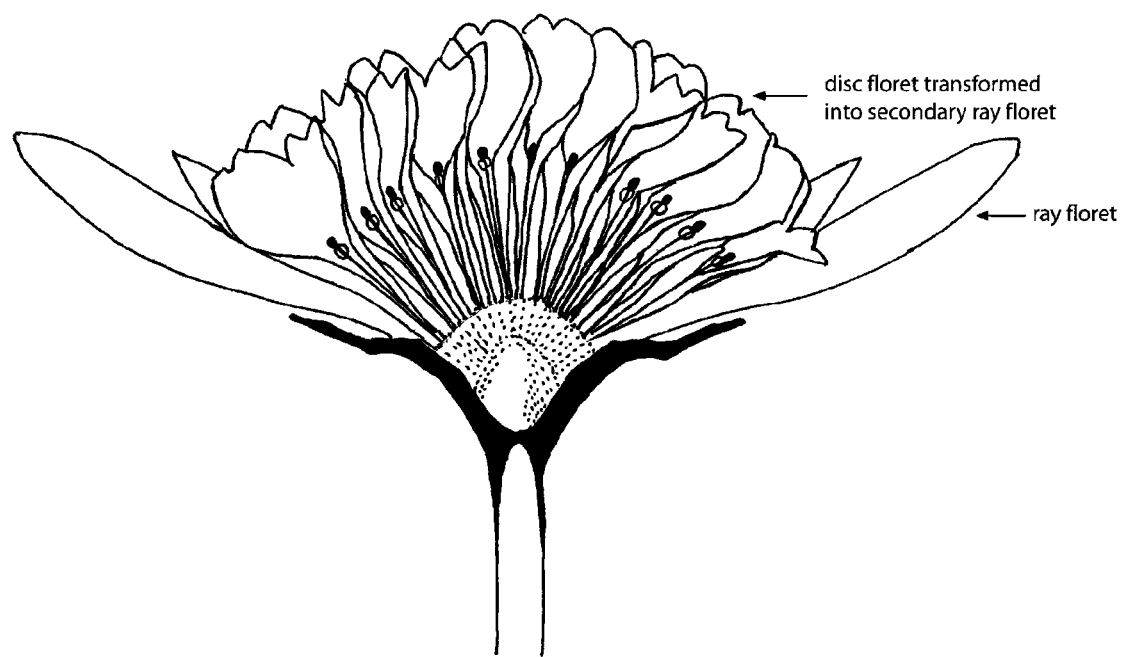
FIG. 6 shows a drawing of a longitudinal cross-section of an inflorescence of an altered flowering *Osteospermum* plant with open disc florets transformed into ligulate florets.
Figure 7:
FIG. 7 shows a whole plant with flowers of genotype OE 2008 248.
Figure 8:
FIG. 8 shows a whole plant with flowers of genotype OE 2008 258.
Figure 9:
FIG. 9 shows a whole plant with flowers of genotype OE 2008 274.
Figure 10:
FIG. 10 shows a whole plant with flowers of genotype OE 2008 285.
Figure 11:
FIG. 11 shows a whole plant with flowers of genotype OE 2008 384.
Figure 12:
FIG. 12 shows a whole plant with flowers of genotype OE 2008 390.
Figure 13:
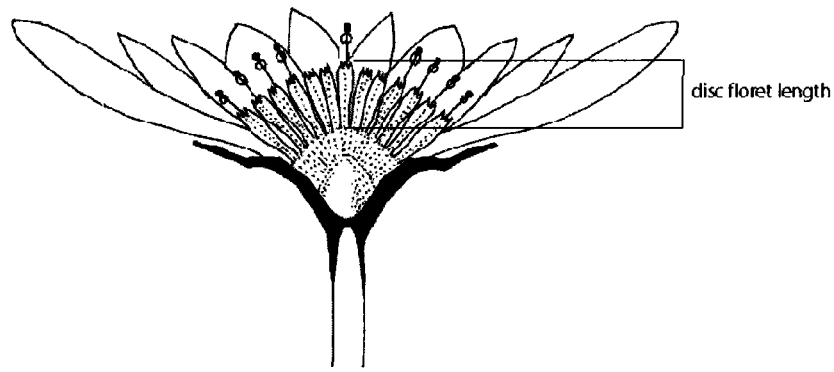
FIG. 13 shows the determination of the disc floret length in a normal flowering *Osteospermum* plant (a), an altered flowering *Osteospermum* plant with enlarged tubular disc florets (b) and an altered flowering *Osteospermum* plant with ligulate florets (c).
Figure 13:
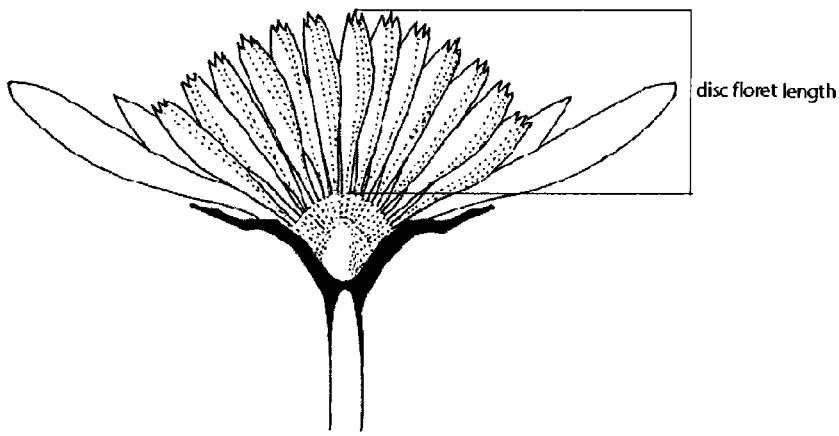
Figure 13:
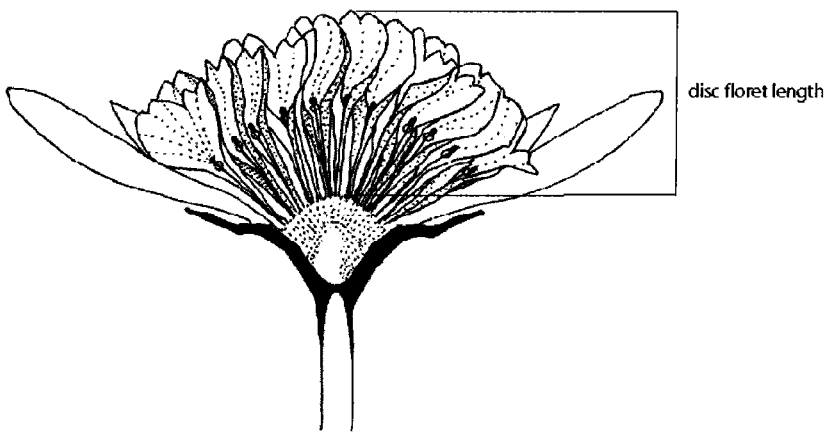

Altered flower. As used herein "altered," "converted" and "enlarged" flower, flowers, flowering, floret, and florets are used interchangeably and refer to Osteospermum or Dimorphoteca plants producing inflorescences with significantly enlarged disc florets. These enlarged disc florets have a length of at least 0.8 cm, whereas the length of disc florets in normal or typical flowering plants is typically less than 0.8 cm. Preferably, the enlarged disc florets have a length of at least 1.3 cm. The enlarged disc florets may still be tubular and enclose the gynoecium and androecium (FIG. 2 and FIG. 5) or the enlarged disc florets may be further extended and open and they may be transformed into ligulate florets (FIG. 3 and FIG. 6) resulting in a double flowering phenotype. All transitions of these phenotypes may occur in plants of the present invention.

AFLP. Amplified fragment length polymorphism (AFLP) is a highly sensitive method for detecting polymorphisms in DNA. Following restriction enzyme digestion of DNA, a subset of DNA fragments is selected for PCR amplification and visualization on a denaturing polyacrylamide gel. The AFLP analysis is described in detail in Nibs et al. (1995) Nucleic Acids Res 23: 4407-14. By AFLP analysis of the plants of the present invention compared to normal flowering plants a marker was identified which can be used to discriminate between normal and altered flowering plants. This marker is a fragment of about 151 nucleotides which is obtained by digesting genomic DNA from the plants with the restriction enzymes EcoRI and MseI, ligating the adapters according to SEQ NOs: 6 to 9 and amplifying DNA from the altered flowering plants with the primers according to SEQ ID NOs: 1 and 2. The 151 bp fragment is only present in the altered flowering plants, but not in the normal flowering plants.

Androecium. Male parts of a plant flower (=collectivity of stamens)

Asexual propagation/Asexual reproduction. Asexual propagation or reproduction means every type of plant propagation apart from seeds, e.g., by cuttings, grafting, division, or regeneration in tissue culture.

Average length. The average length of e.g. disc florets on an Osteospermum inflorescence is determined by measuring the smallest and the longest disc floret length and calculating their average which is then taken as average length of the disc floret of that respective inflorescence.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bulked Segregant Analysis. A rapid mapping strategy suitable for monogenic qualitative traits. When DNA of ten plants is bulked into one pool, all alleles must be present. Two bulked pools of segregants differing for one trait will differ only at the locus harboring that trait.

Capitulum. Capitulum refers to an inflorescence in the form of a central disc of sessile flowers called disc florets and an outer ring of petal-like structures called ray florets. The disc florets are generally perfect while the ray florets are generally imperfect.

Cell. Cell as used herein includes a plant cell, whether isolated, in tissue culture, or incorporated in a plant or plant part.

Chimera. A chimera or a chimeric plant is a plant that consists of two or more genetically distinct groups of cells. The genetic distinctness usually originates from a mutation.

Corolla. The collective term for all the petals on a single flower. The single flower in this case may be a disc floret or a ray floret.

Daminozide. Is a plant growth regulator having the chemical structure N-(dimethylamino)succinamic acid which is marketed under the name Daminozide, Alar, Kylar or B9.

Dimorphoteca plant. Refers to a plant of the genus Dimorphoteca, for example Dimorphoteca sinuata or Dimorphoteca pluvialis.

Disc floret. One of the small tubular, actinomorphic florets which make up the central part of the flower head in Compositae or Asteraceae plants. The enlarged disc florets of the present invention may still be tubular or be transformed into ligulate florets.

Dominant inheritance. Refers to a mode of inheritance in which the phenotype of a certain characteristic or trait is determined by a dominant allele.

Dominant allele. The phenotype of a dominant allele is visible in a heterozygous genotype.

Double flower. In the Asteraceae or Compositae plant family, the term "Double flower" or "Semi-double flower" refers to inflorescences which have more than one whorl of ray florets. In completely "double-flowering" plants, all disc florets are transferred into ray florets, whereas in "semi-double-flowering" plants, only several whorls of disc florets are mutated into ray florets.

Embryo. The embryo is the small juvenile plant contained within a mature seed.

Embryo rescue. Refers to a technique intended to rescue inherently weak, immature or hybrid embryos to prevent degeneration of the embryos which otherwise would have died in a later stage of development. The rescued embryos are then grown on a suitable medium.

Flower. A flower is the reproductive structure found in flowering plants. Single flowers stand on petioles or maybe arranged in clusters forming an inflorescence standing on a stem.

$F_2$. The "$F_2$" symbol denotes a generation resulting from the selfing of the $F_1$ generation along with selection for type and rogueing of off-types. The "F" number is a term commonly used in genetics, and designates the number of the filial generation. The "$F_2$" generation denotes the offspring resulting from the selfing or self mating of members of the generation having the next lower "F" number, viz. the $F_1$ generation.

Gamete. A gamete is a cell that fuses with another gamete during fertilization in organisms that reproduce sexually. In plants the gametes are the ovule and pollen cell.

Gene. As used herein, "gene" refers to a segment of nucleic acid. A gene can be introduced into a genome of a species, whether from a different species or from the same species, using transformation or various breeding methods.

Gene-environment interaction/Genotype-environment interaction. Refers to the phenotypic effect of interactions between genes and the environment.

Genetic transformation. Refers to the genetic alteration of a cell resulting from the uptake, genomic incorporation, and expression of foreign genetic material.

Gene converted (Conversion). Gene converted (conversion) plants refers to plants which are developed by a plant breeding technique called backcrossing wherein essentially all of the desired morphological and physiological characteristics of a plant are recovered in addition to the one or more genes transferred into the plant via the backcrossing technique, genetic engineering or mutation.

Genotype. Refers to the genetic constitution of a cell or organism.

Gynoecium. Ovule-producing parts of a plant flower

Heterozygous. Refers to a genetic constitution in which the corresponding alleles of a certain gene locus are different.

Homozygous. Refers to a genetic constitution in which the corresponding alleles of a certain gene locus are identical.

Inbreeding depression. Inbreeding depression is the reduced fitness in a given population as a result of breeding of close relatives or in plants also resulting from self-pollination.

INDEL. Indel describes a special mutation class, i.e. a mutation resulting in a colocalized insertion and deletion and a net gain or loss in nucleotides.

Inflorescence. A group or cluster of flowers arranged on a stem that is composed of a main branch or an arrangement of branches. In a normal flowering *Osteospermum* the inflorescence is formed by disc florets surrounded by ray florets.

Intergeneric cross. Intergeneric cross means the sexual hybridization of two individuals, each from a different genus such as *Osteospermum* and *Dimorphoteca*.

Intergeneric hybrid. Intergeneric hybrid means a plant of the $F_1$ generation resulting from an intergeneric cross or a cross between two different genera.

Interspecific cross. Interspecific cross means the sexual hybridization of two individuals, each from different species.

Interspecific hybrid. Interspecific hybrid means a plant of the $F_1$ generation resulting from an interspecific cross or a cross between two different species.

Keepability. Keepability refers to the period between the complete opening of the flowers, i.e. when the flower buds start showing the color of the petals and the wilting of the flowers, i.e. when two-three petals started showing aged symptoms and flower started appearing dull. Alternatively, the complete opening of the flowers is the time point at which the ray florets are unfolded and the complete loss of the flowers is characterized by the folding of the ray florets and the concomitant bending of the flower stalk. For each genotype the difference between the day the flower opened and the day it wilted is called the flower keepability. The keepability of the plants of the present invention has been determined under green house conditions in Central Europe (e.g. in Stuttgart). Under these conditions, the mean keepability of the normal flower plants was approximately 12 days, whereas the average keepability of the plants of the present invention was at least 15 days, preferably 16 or 17 days. Alternatively, the keepability of the plants of the present invention has been determined in the field in summer in Central Europe (e.g. in Stuttgart), i.e. under long-day conditions with changing environmental conditions. The altered flower plants of the present invention were grown isolated from the plants of the normal flowers to avoid pollination of the altered flower plants by the normal flower plants. Under these conditions, the keepability of the normal flower plants was less than ten days, for example eight or nine days and the keepability of the plants of the present invention was at least 15 days, preferably 16 or 17 days, more preferably 18 or 19 days and most preferably 20 days.

KLEDF allele. The allele which is responsible for the development of the altered flower phenotype of the present invention, i.e. a phenotype wherein at least one inflorescence has at least one disc floret with a length of at least 0.8 cm. If the KLEDF allele is present, the plant will show the phenotype of the present invention. The presence of the KLEDF allele can be determined by means of molecular marker technology, e.g. by the AFLP technique. When applying this technique to the plants of the present invention, genomic DNA of a plant of the present invention can be digested with EcoRI and MseI, adapters according to SEQ ID NOs: 6 to 9 are ligated to the fragments and the DNA is amplified by PCR using the primers according to SEQ ID NO: 1 and 2. This amplification yields a fragment of about 151 nucleotides which is present in the altered flowering plants, but not in the normal flowering plants.

Linkage/Genetic Linkage. Describes the tendency of certain genetic loci or alleles to be inherited together. Genetic loci on the same chromosome are physically close to one another and tend to stay together during meiosis, and are thus genetically linked.

Locus. A locus confers one or more traits such as, for example, herbicide tolerance, insect resistance, disease resistance, flower color, flower shape, plant height, etc. The trait may be, for example, conferred by a naturally occurring gene introduced into the genome of the plant by backcrossing, a natural or induced mutation, or a transgene introduced through genetic transformation techniques. A locus may comprise one or more alleles integrated at a single chromosomal location.

M0. The M0 generation is the generation treated with a mutagen.

Meiosis. Refers to the process of reduction division in which the number of chromosomes per cell is divided in half and which results in the formation of the gametes. Meiosis is essential for the sexual reproduction.

Molecular Marker/Genetic Marker. A molecular marker or genetic marker is a fragment of a DNA sequence that is associated to a part of the genome and linked to a certain phenotype such as the altered flowering phenotype of the present invention. One molecular marker described herein is a fragment of about 151 bp which was identified by the AFLP technique and which is only present in the altered flowering plants, but not in the normal flowering plants.

Monogenic inheritance. Refers to a mode of inheritance in which the phenotype of a certain characteristic or trait is determined by a single gene.

Mutation. Mutations are changes in the DNA sequence of a cell's genome and are caused by mutagens like radiation or chemicals as well as by errors that occur during DNA replication.

Mutation treatment. Refers to any treatment which is intended to introduce mutations in the DNA sequence of a cell's genome, in particular the treatment with radiation such as Gamma-irradiation and the treatment with chemical mutagens such as ethylmethanesulfonate (EMS).

Figure 1:
FIG. 1 shows a close-up of a normal flowering *Osteospermum* plant.
Figure 4:
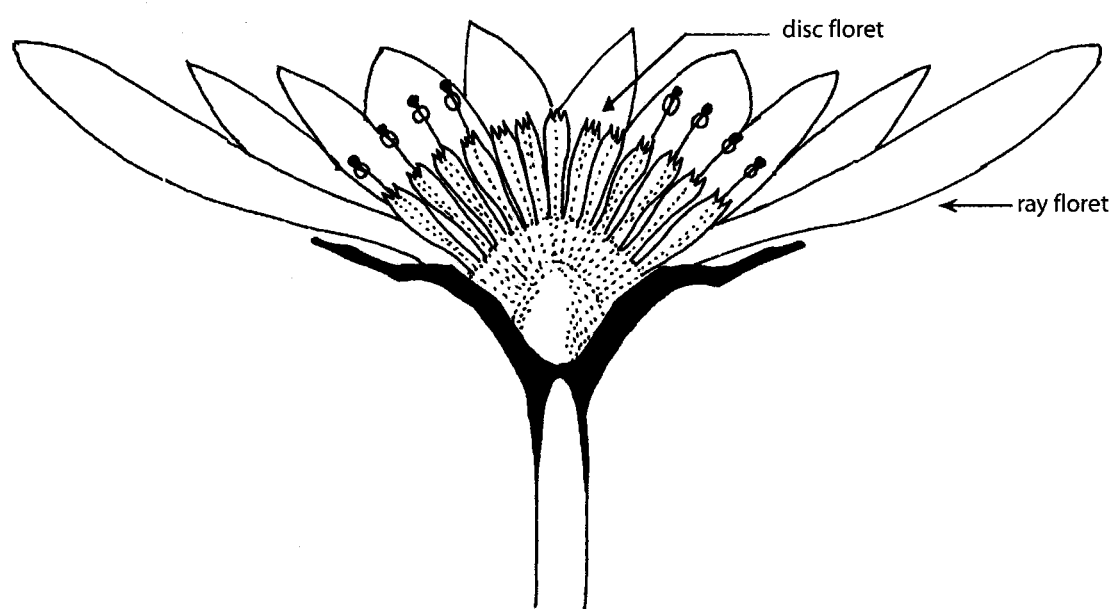
FIG. 4 shows a drawing of a longitudinal cross-section of an inflorescence of a normal flowering *Osteospermum* plant.

Normal flower. As used herein "normal," "typical," "usual," and "regular" flower, flowers, flowering, floret, and florets are used interchangeably and refer to currently available commercial *Osteospermum* and *Dimorphoteca* plants which produce inflorescences with tubular disc florets enclosing but standing below the mature gynoecium and androecium, the disc floret shaving an average length of less than 0.8 cm (see FIG. 1 and FIG. 4).

*Osteospermum* plant. Refers to plants of the genus *Osteospermum*, for example *Osteospermum ecklonis* or *Osteospermum jucundum*.

PCR (Polymerase Chain Reaction). PCR describes a molecular biological method for amplifying a nucleic acid molecule, essentially comprising the steps of denaturation of the DNA, annealing of the primers and elongation of the primers with a thermostable DNA polymerase, using the nucleic acid sequence to be amplified as a template.

Phenotype. Refers to any observable characteristic or trait of an organism like flower color, plant size, etc.

Plant. As used herein, the term "plant" includes reference to an immature or mature whole plant, including a plant from which seed or anthers have been removed. Seed or embryo that will produce the plant is also considered to be the plant.

Plant growth regulator. Refers to a natural or synthetic compound which can regulate plant growth, including anti-auxins, auxins, cytokinins, defoliants, ethylene inhibitors, ethylene releasers, gametocides, gibberellins, growth inhibitors, morphactins, growth retardants and growth stimulators. Within the present invention, preferably a growth retardant and more preferably daminozide is used to increase seed yield in an altered flowering plant.

Plant Parts. As used herein, the term "plant parts" (or an *Osteospermum* or *Dimorphoteca* plant, or a part thereof) includes, but is not limited to, protoplasts, leaves, stems, roots, root tips, anthers, pistils, seed, embryo, pollen, ovules, cotyledon, hypocotyl, capitulum, ray petal/floret, disc petal/floret, shoot, tissue, petiole, cells, meristematic cells, and the like.

Pollination. Pollination is the process by which pollen is transferred in plants, thereby enabling fertilization and sexual reproduction.

Polymorphism. In plant biology polymorphism occurs when two or more clearly different phenotypes exist in the same plant population, resulting from multiple alleles of a gene within this population.

Primer. A primer is a short, single stranded nucleic acid which serves as the starting point for DNA synthesis, e.g. in PCR.

Progeny. As used herein, includes an $F_1$ *Osteospermum* or *Dimorphoteca* plant or a hybrid plant of *Osteospermum* or *Dimorphoteca* produced from the cross of two *Osteospermum* or *Dimorphoteca* plants and progeny. It further includes, but is not limited to, subsequent $F_2$, $F_3$, $F_4$, $F_5$, $F_6$, $F_7$, $F_8$, $F_9$, and $F_{10}$ generational crosses with plants of the same generation.

Protoplast fusion/Somatic fusion. Refers to a method in plants by which protoplasts (i.e., plant cells without cell walls) from two different plants are fused together to form a new hybrid plant with characteristics of both.

Quantitative Trait Loci (QTL). Quantitative trait loci (QTL) refer to genetic loci that control to some degree numerically representable traits that are usually continuously distributed.

Ray floret. A ray floret or ligulate floret, is one of the outer, irregular florets in the flower heads of some Compositae or Asteraceae plants. Colloquial in Asteraceae or Compositae plants, the ray florets are called petals.

Recessive inheritance. Refers to a mode of inheritance in which the phenotype of a certain characteristic or trait is determined by a recessive allele.

Recessive allele. The phenotype of a recessive allele is visible only in a homozygous genotype.

Regeneration. Regeneration refers to the development of a plant from tissue culture.

Segregating Progeny. Refers to a seedling progeny, in which the phenotypic traits and the respective genes divide onto the single individuals according to Mendelian rules.

Selection. Refers to the process of choosing from among the progeny of a crossing or the plants resulting from transformation, protoplast fusion or embryo rescue those plants which display the desired phenotype and/or genotype. Within the meaning of the present invention, the desired phenotype is the altered flower phenotype as described herein and the desired genotype is characterized by the presence of the KLEDF allele.

Sexual propagation/Sexual reproduction. Refers to the propagation of plants from seeds.

SNP. A single-nucleotide polymorphism (SNP) is a DNA sequence variation occurring when a single nucleotide—A, T, C, or G—in the genome (or other shared sequence) differs between members of a biological species or paired chromosomes in an individual. It has been found that in the altered flowering plants of the present invention the N within the sequence TTTGANAAAG (SEQ ID NO: 10) in a DNA fragment amplified with primers according to SEQ ID NOs: 3 and 4 is C, whereas in normal flowering plants N is T. In some altered flowering plants the nucleotide substitution is on position 73 of the nucleic acid sequence according to SEQ ID NO: 5.

Transformation. Refers to a process wherein a polynucleotide which is not in its natural context, e.g. linked to a promoter with which it is not naturally linked, or which is isolated from the other parts of the gene with which it is normally linked, is transferred into a plant. Suitable transformation methods include, but are not limited to, Agrobacterium mediated transformation, particle bombardment and electroporation.

DETAILED DESCRIPTION OF THE INVENTION

The altered flowering plants of the present invention preferably have substantially all altered flowers resulting in a double-flowering phenotype. However, under certain circumstances, only part of the disc florets may be enlarged or only some of the inflorescences are altered inflorescences. This means that the number of enlarged disc florets per inflorescence may vary from only a few to more than 100 per inflorescence. All previously known *Osteospermum* and *Dimorphoteca* plants do not have the altered flowers of the present invention. Unexpectedly, the mutant allele of the present invention results in inflorescences having disc florets which are significantly enlarged compared to the disc florets of previously known *Osteospermum* and *Dimorphoteca* inflorescences.

The new altered flowering phenotype of the present invention resulting from a mutant allele does not necessarily eliminate the fertility of the flower. The anthers, which are located in the disc floret may be fertile and produce pollen. However, since the anthers are covered by the enlarged disc florets, the pollen is not visible and not freely available for insects and stigmas are covered by enlarged disc florets and are therefore not easily accessible for pollinating insects. Therefore, in the field plants with the altered flowering phenotype show significantly reduced seed set originating from insect pollination and consequently an extended flower keepability. Seed set usually originates from the gynoecium located at the base of the ray florets, whereas the disc floret gynoecium seems to be degenerated in both normal flowering plants and the new altered flowering plants.

The present invention encompasses *Osteospermum* plants exhibiting an altered flower phenotype and having at least one enlarged disc floret, preferably at least two, five, eight, ten, twelve, 15, 18 or 20 enlarged disc florets, more preferably at least 22, 25, 28, 30, 35, 38 or 40 enlarged disc florets, even more preferably at least 42, 45, 48, 50, 52, 55, 58 or 60 enlarged disc florets, particularly preferably at least 62, 65, 68, 70, 72, 73, 75, 78 or 80 enlarged disc florets and even more preferably 82, 84, 85, 86, 88, 89, 90, 92, 94, 95, 96, 98, 100 or 108 enlarged disc florets. Most preferably, all disc florets of an inflorescence are enlarged.

The enlarged disc florets of the present invention have a length of at least 0.8 cm, 0.9 cm, 0.96 cm, 1.00 cm, 1.01 cm, 1.15 cm, 1.21 cm, 1.26 cm, 1.29 cm, 1.30 cm, 1.31 cm, 1.34 cm, 1.38 cm, 1.40 cm, 1.42 cm, 1.45 cm, 1.49 cm, 1.51 cm, 1.52 cm, 1.55 cm, 1.57 cm, 1.61 cm, 1.63 cm, 1.64 cm, 1.66 cm, 1.69 cm, 1.70 cm, 1.80 cm, 1.90 cm, 2.0 cm, 2.01 cm, 2.1 cm, 2.16 cm, 2.19 cm, 2.20 cm, 2.23 cm, 2.26 cm, 2.28 cm, 2.30 cm, 2.33 cm, 2.36 cm, 2.37 cm, 2.39 cm, 2.4 cm, 2.5 cm, 2.6 cm, 2.7 cm, 2.8 cm, 2.9 cm, 3.0 cm, 3.1 cm, 3.2 cm, 3.3 cm, 3.4 cm, 3.5 cm, 3.6 cm, 3.7 cm, 3.8 cm, 3.9 cm, 4.0 cm, 4.1 cm, 4.2 cm, 4.3 cm, 4.4 cm, 4.5 cm, 4.6 cm, 4.7 cm, 4.8 cm, 4.9 cm, 5.0 cm, 5.1 cm, 5.2 cm, 5.3 cm, 5.4 cm, 5.5 cm, 5.6 cm, 5.7 cm, 5.8 cm, 5.9 cm and 6.0 cm, including all integers and fractions thereof.

Alternatively or additionally, the average length of the shortest and the longest disc floret on at least one inflorescence of the plant is at least 1.21 cm, 1.22 cm, 1.23 cm, 1.24 cm, 1.25 cm, 1.26 cm, 1.27 cm, 1.28 cm 1.29 cm, 1.30 cm, 1.31 cm, 1.34 cm, 1.38 cm, 1.40 cm, 1.42 cm, 1.45 cm, 1.49 cm, 1.51 cm, 1.52 cm, 1.55 cm, 1.57 cm, 1.61 cm, 1.63 cm, 1.64 cm, 1.66 cm, 1.69 cm, 1.70 cm, 1.80 cm, 1.90 cm, 2.0 cm, 2.01 cm, 2.1 cm, 2.16 cm, 2.19 cm, 2.20 cm, 2.23 cm, 2.26 cm, 2.28 cm, 2.30 cm, 2.33 cm, 2.36 cm, 2.37 cm, 2.39 cm, 2.4 cm, 2.5 cm, 2.6 cm, 2.7 cm, 2.8 cm, 2.9 cm, 3.0 cm, 3.1 cm, 3.2 cm, 3.3 cm, 3.4 cm, 3.5 cm, 3.6 cm, 3.7 cm, 3.8 cm, 3.9 cm, 4.0 cm, 4.1 cm, 4.2 cm, 4.3 cm, 4.4 cm, 4.5 cm, 4.6 cm, 4.7 cm, 4.8 cm, 4.9 cm, 5.0 cm, 5.1 cm, 5.2 cm, 5.3 cm, 5.4 cm, 5.5 cm, 5.6 cm, 5.7 cm, 5.8 cm, 5.9 cm and 6.0 cm, including all integers and fractions thereof.

In some embodiments of the present invention, the average length of at least one disc floret is between 0.8 cm and 6.0 cm, between 0.8 cm and 5.8 cm, between 0.8 cm and 5.5 cm, between 0.8 cm and 5.2 cm, between 0.8 cm and 5.0 cm, between 0.8 cm and 4.8 cm, between 0.8 cm and 4.5 cm, between 0.8 cm and 4.2 cm, between 0.8 cm and 4.0 cm, between 0.8 cm and 3.8 cm, between 0.8 cm and 3.5 cm, between 0.8 cm and 3.2 cm, between 0.8 cm and 3.0 cm, between 0.8 cm and 2.8 cm, between 0.8 cm and 2.5 cm, between 0.8 cm and 2.4 cm, between 0.8 cm and 2.3 cm, between 0.8 cm and 2.2 cm, between 0.8 cm and 2.1 cm, between 0.8 cm and 2.0 cm, between 0.8 cm and 1.9 cm, between 0.8 cm and 1.8 cm, between 0.8 cm and 1.7 cm, between 0.8 cm and 1.6 cm, between 0.8 cm and 1.4 cm, between 0.8 cm and 1.3 cm or between 0.8 cm and 1.2 cm.

In some embodiments of the present invention, the average length of the shortest and the longest disc floret of at least one inflorescence is between 0.8 cm and 6.0 cm, between 0.8 cm and 5.8 cm, between 0.8 cm and 5.5 cm, between 0.8 cm and 5.2 cm, between 0.8 cm and 5.0 cm, between 0.8 cm and 4.8 cm, between 0.8 cm and 4.5 cm, between 0.8 cm and 4.2 cm, between 0.8 cm and 4.0 cm, between 0.8 cm and 3.8 cm, between 0.8 cm and 3.5 cm, between 0.8 cm and 3.2 cm, between 0.8 cm and 3.0 cm, between 0.8 cm and 2.8 cm, between 0.8 cm and 2.5 cm, between 0.8 cm and 2.4 cm, between 0.8 cm and 2.3 cm, between 0.8 cm and 2.2 cm, between 0.8 cm and 2.1 cm, between 0.8 cm and 2.0 cm, between 0.8 cm and 1.9 cm, between 0.8 cm and 1.8 cm, between 0.8 cm and 1.7 cm, between 0.8 cm and 1.6 cm, between 0.8 cm and 1.4 cm, between 0.8 cm and 1.3 cm or between 0.8 cm and 1.2 cm.

In other embodiments of the present invention the average length of at least one disc floret is between 1.0 cm and 6.0 cm, between 1.1 cm and 6.0 cm, between 1.2 cm and 6.0 cm, between 1.3 cm and 6.0 cm, between 1.4 cm and 6.0 cm, between 1.5 cm and 6.0 cm, between 1.6 cm and 6.0 cm, between 1.7 cm and 6.0 cm, between 1.8 cm and 6.0 cm, between 1.9 cm and 6.0 cm, between 2.0 cm and 6.0 cm, between 2.1 cm and 6.0 cm, between 2.2 cm and 6.0 cm, between 2.5 cm and 6.0 cm, between 2.7 cm and 6.0 cm, between 3.0 cm and 6.0 cm, between 3.2 cm and 6.0 cm, between 3.5 cm and 6.0 cm, between 3.8 cm and 6.0 cm, between 4.0 cm and 6.0 cm, between 4.2 cm and 6.0 cm, between 4.5 cm and 6.0 cm, between 4.8 cm and 6.0 cm, between 5.0 cm and 6.0 cm, between 5.2 cm and 6.0 cm, between 5.5 cm and 6.0 cm or between 5.8 cm and 6.0 cm.

In other embodiments of the present invention the average length the longest and the shortest disc floret of at least one inflorescence is between 1.0 cm and 6.0 cm, between 1.1 cm and 6.0 cm, between 1.2 cm and 6.0 cm, between 1.3 cm and 6.0 cm, between 1.4 cm and 6.0 cm, between 1.5 cm and 6.0 cm, between 1.6 cm and 6.0 cm, between 1.7 cm and 6.0 cm, between 1.8 cm and 6.0 cm, between 1.9 cm and 6.0 cm, between 2.0 cm and 6.0 cm, between 2.1 cm and 6.0 cm, between 2.2 cm and 6.0 cm, between 2.5 cm and 6.0 cm, between 2.7 cm and 6.0 cm, between 3.0 cm and 6.0 cm, between 3.2 cm and 6.0 cm, between 3.5 cm and 6.0 cm, between 3.8 cm and 6.0 cm, between 4.0 cm and 6.0 cm, between 4.2 cm and 6.0 cm, between 4.5 cm and 6.0 cm, between 4.8 cm and 6.0 cm, between 5.0 cm and 6.0 cm, between 5.2 cm and 6.0 cm, between 5.5 cm and 6.0 cm or between 5.8 cm and 6.0 cm.

In other embodiments of the present invention the average length of at least one disc floret is between 1.0 cm and 3.0 cm, between 1.0 cm and 2.9 cm, between 1.0 cm and 2.8 cm, between 1.0 cm and 2.7 cm, between 1.0 cm and 2.6 cm, between 1.0 cm and 2.5 cm, between 1.0 cm and 2.4 cm, between 1.0 cm and 2.3 cm or between 1.0 cm and 2.2 cm.

In other embodiments of the present invention the average length of the longest and the shortest disc floret of at least one inflorescence is between 1.0 cm and 3.0 cm, between 1.0 cm and 2.9 cm, between 1.0 cm and 2.8 cm, between 1.0 cm and 2.7 cm, between 1.0 cm and 2.6 cm, between 1.0 cm and 2.5 cm, between 1.0 cm and 2.4 cm, between 1.0 cm and 2.3 cm or between 1.0 cm and 2.2 cm.

In still further embodiments of the present invention the average length of the shortest and the longest disc floret of at least one inflorescence is between 1.25 cm and 3.0 cm, between 1.25 cm and 2.9 cm, between 1.25 cm and 2.8 cm, between 1.25 cm and 2.7 cm, between 1.25 cm and 2.6 cm, between 1.25 cm and 2.5 cm, between 1.25 cm and 2.4 cm, between 1.25 cm and 2.3 cm or between 1.25 cm and 2.2 cm. In yet further embodiments of the present invention the average length of the shortest and the longest disc floret of at least one inflorescence is between 1.4 cm and 2.4 cm, between 1.4 cm and 2.2 cm, between 1.4 cm and 2.0 cm, between 1.4 cm and 1.9 cm or between 1.4 cm and 1.8 cm.

The present invention further comprises altered flowering *Osteospermum* plants wherein the average length of the longest and the shortest disc floret of at least one inflorescence is 1.45 cm, 1.5 cm, 1.55 cm, 1.6 cm or 1.7 cm.

Figure 14:
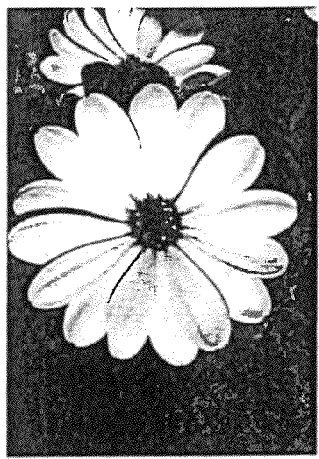
FIG. 14, upper panel, shows a normal flowering *Osteospermum* plant (1), an altered flowering *Osteospermum* plant with enlarged tubular disc florets (2) and an altered flowering *Osteospermum* plant with ligulate florets (3). The lower panel (4) is a photograph showing individual disc florets and the method of determining the corolla length of the disc florets.
Figure 14:
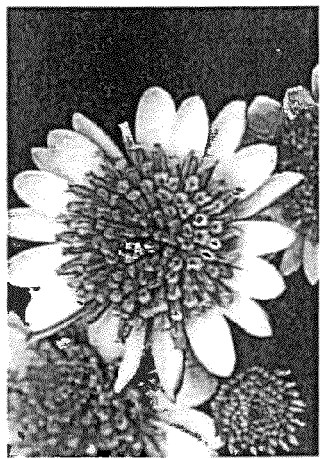
Figure 14:
Figure 14:
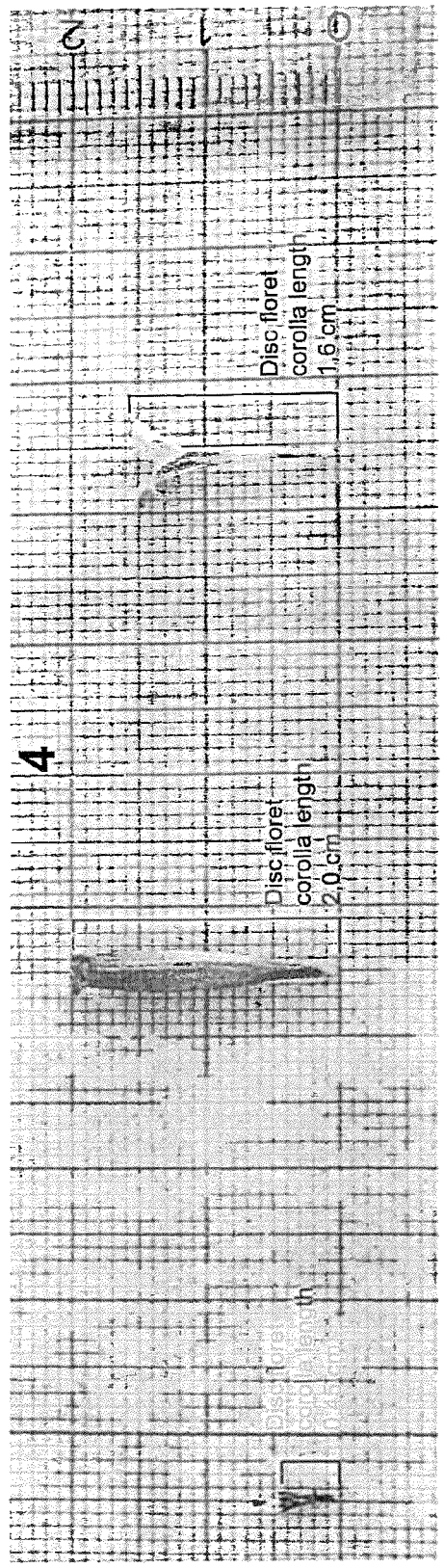

The length of the disc florets is determined by removing the disc florets from the inflorescence and measuring the length from the base of the disc florets to the top (see FIG. 14). It is possible to determine the length of all disc florets of an inflorescence, but in cases where the appearance of the disc florets is uniform, it is sufficient to determine the length of e.g. ten disc florets and take the average value of the length. Alternatively, the average value of the smallest and longest disc floret of an inflorescence is determined. In preferred embodiments, the length of the disc floret refers to the length of the disc floret corolla and therefore does not include the length of the anthers which poke out of the corollas in normal flowering plants.

In still another embodiment of the present invention the ratio of the average length of the longest and the shortest ray floret of at least one inflorescence to the average length of the longest and the shortest disc floret of at least one inflorescence is less than 2.0, preferably less than 1.95, more preferably less than 1.9 and most preferably less than 1.88. In another embodiment the ratio of the average length of the longest and the shortest ray floret of at least one inflorescence to the average length of the longest and the shortest disc floret of at least one inflorescence is between 1.2 and 2.0, preferably between 1.25 and 1.95, more preferably between 1.3 and 1.9 and most preferably between 1.35 and 1.88.

In yet other embodiments of the present invention the average length of the longest and the shortest disc floret of an inflorescence is at least 1.25 cm and the ratio of the average length of the longest and the shortest ray floret of at least one inflorescence to the average length of the longest and the shortest disc floret of at least one inflorescence is less than 2.0. Alternatively, the average length of the longest and the shortest disc floret of an inflorescence is between 1.25 cm and 2.0 cm and the ratio of the average length of the longest and the shortest ray floret of at least one inflorescence to the average length of the longest and the shortest disc floret of at least one inflorescence is between 1.2 and 2.0. In a further embodiment, the average length of the longest and the shortest disc floret of at least one inflorescence is between 1.4 cm and 1.8 cm and the ratio of the average length of the longest and the shortest ray floret of at least one inflorescence to the average length of the longest and the shortest disc floret of at least one inflorescence is between 1.35 and 1.88.

The plants of the present invention may also be obtained by mutation treatment with Gamma-irradiation dosages up to 500 Gy, incubation periods of up to several hours, repeated irradiation treatments and/or the irradiation of pollen or flower buds. In addition to Gamma-irradiation, X ray or UV radiation may also be applied. Furthermore, the plants may be treated with a chemical mutagen, e.g. with ethyl methanesulfonate (EMS), as it is e.g. described for the induction of altered flower colors and flower shapes in *Petunia hybrida* (Gerats T. and Strommer J. (eds.), Petunia—Evolutionary, Developmental and Physiological Genetics, Springer Life Sciences, 2nd. ed., XXII (2009); Harten van, A. M., Mutation Breeding: Theory and Practical Applications, Cambridge University Press (1998)).

The new altered flowering *Osteospermum* plants are genetically stable, as evidenced by the stability of the altered-type phenotype through asexual propagation and the transmission of this trait to the progeny after sexual crosses.

The evaluation of further segregating progeny combined with the application of molecular marker technology has clarified the inheritance of the new altered flower phenotype in *Osteospermum* in more detail. To map the mutant KLEDF allele, a segregating $F_2$ or backcross population of plants showing the altered flower phenotype derived from a cross between a normal and an altered flowering plant was produced. On this segregating population a molecular marker analysis was performed to screen for polymorphism between the parents and the normal flowering genotypes and the altered flowering genotypes, respectively. The aim was to identify markers which are polymorphic in both the parents and differentiate between the normal and the altered flowering genotypes. For this analysis different molecular marker techniques like the AFLP and SNP technique were used. With these polymorphic DNA markers a linkage analysis is performed on the segregating progeny to identify the chromosomal locations of the KLEDF allele.

The AFLP analysis has shown that a fragment of about 151 nucleotides which is obtained by digesting genomic DNA from the plants with the restriction enzymes EcoRI and MseI, ligating the adapters according to SEQ ID NOs: 6 to 9 and amplifying DNA from the altered flowering plants with the primers according to SEQ ID NOs: 1 and 2 can only be detected in plants with an altered flowering phenotype but not in plants with a normal flowering phenotype.

Further, the SNP analysis showed that the N within the sequence TTTGANAAAG (SEQ ID NO: 10) in a DNA fragment amplified with primers according to SEQ ID NOs: 3 and 4 is C, whereas in normal flowering plants N is T.

The analysis of the altered flowering plants of the present invention has also shown a reduced seed yield in these plants. However, the seed yield could be increased and the phenotype of the plants could be transformed almost to the normal flowering phenotype by treating the altered flowering plants with a plant growth regulator such as daminozide. The plants treated in this way could be used in crosses. Suitable concentrations of the plant growth regulator, preferably daminozide, are 0.05% to 0.4%, preferably 0.1% to 0.3%, more preferably 0.15% to 0.25% and most preferably 0.2%.

EXAMPLES

Example 1

Development of an Altered *Osteospermum* Flower Phenotype

In spring 2007 in a proprietary population of *Osteospermum* plants, a single plant was found which showed a slightly modified flower phenotype. A more detailed analysis of the flowers on this plant showed that on some of the flowers, the disc florets were elongated and covered the androecium and the gynoecium, whereas in the normal flowers on the same plant the androecium as well as the gynoecium were standing above the disc florets. The phenotype of this plant was identified as a novelty with a certain potential to be useful for the development of a new flower type within the genus *Osteospermum*. Therefore, further analyses on this plant were performed.

Firstly, it had to be shown if this altered phenotype was the result of a genetic mutation or if it was a modification induced by environmental conditions like the extra whorl of ray florets described above. For this purpose, cuttings from this plant were taken repeatedly, rooted, and grown to flowering plants. Among these plant populations, three different groups of individuals were detected. The first group of individuals was comprised of plants which exhibited only normal flowers, whereas the second group of plants exhibited flowers with the altered phenotype. A further third group of plants consisted of plants which exhibited both types of flowers, the normal type as well as the altered type. This result indicated that the altered flower type could be transmitted by asexual propagation, but it further indicated that this plant was a chimera.

Next, it had to be shown that the new flower type could be transmitted through sexual propagation. Therefore a breeding program with this altered flowering plant was designed. The sexual transmission of the altered phenotype may depend on the genetic background of the respective crossing parent. Therefore these were carefully selected by their phenotypes and also by their genotypes, making use of a genetic distance analysis which had been performed in the framework of a research project by Gawenda and Debener reported in 2009

(Gawenda, I. and Debener, T., Genetic diversity of *Osteospermum* genotypes analysed by AFLP and chloroplast SSR markers, *Europ. J. Hort. Sci.,* 74 (2), 86-94 (2009)). The normal-flowering *Osteospermum* genotypes, which were used as crossing parents, were all proprietary assortment varieties or breeding lines.

A first series of pollinations was performed wherein the plant exhibiting the modified flower type was used as a male as well as a female parent. The flowers of the female crossing parents were emasculated before mature pollen appeared. On average, 2 days after emasculation, the stigmas at the base of the ray florets extend which indicates that they are ready for pollination. At this stage they were pollinated repeatedly with pollen from the respective male parent. The use of the altered flowering plant as the male parent needed specific skills of the pollinators, because the pollen had to be collected carefully at the base of the altered disc florets. About 4 weeks after pollination the seeds were ready for harvesting. In total, 32 crossing combinations had been performed, but only 16 of the combinations produced seeds. In total, almost 5,000 seeds were harvested and sown.

For sowing the seeds were soaked in a solution of 10% PEG for 4 hours, the solution was washed off, and the seeds were sown in standard seedling substrate. Germination started after about one week. Three weeks after sowing, when the first pair of leaves had developed, the seedlings were transplanted. Three weeks after transplanting the seedlings were planted into 11 cm diameter pots and grown according to standard protocols. First flowering started about 10 weeks after potting.

The seedling populations were evaluated over a period of 4 weeks mainly focusing on the selection of plants exhibiting the altered flower-type. The progeny comprised 2,459 flowering plants in total. In all progeny plants were selected which showed an altered flowering phenotype, meaning that these plants had at least one elongated disc floret. The number of altered flowering plants compared to the total number of seedlings varied among the different progeny. Since the first altered flowering plant, which was used as a breeding parent, was a chimera, meaning it produced altered flowers as well as normal flowers on one plant, the segregation pattern was unpredictable, although only altered flowers had been used for pollination. Table 1 summarizes the number of altered flowering and normal flowering plants for 9 progeny, which comprised enough seedlings for a segregation analysis. Unexpectedly, the frequency of seedlings exhibiting altered flowers was in all combinations far from that corresponding to a 1:1-segregation, the expected segregation in case of a dominant inheritance, which is shown by the respective $\chi^2$, values (Table 1). Also unexpectedly none of the progeny exhibited exclusively normal flowering plants, which would be expected in the case of a recessive inheritance. Furthermore, the data in Table 1 show that the altered flowering trait is not linked to flower color.

In Table 1, column 1 shows the color of the ray florets of the respective crossing partners exhibiting normal flower types. Columns 2 through 5 show the number of plants producing normal inflorescences for each color and the total number of plants. Columns 6 through 9 show the number of plants producing altered inflorescences for each color and the total number of plants with altered inflorescences. Columns 10 through 13 show the total number of plants for each color as well as the total number of evaluated seedlings per progeny. Finally, column 14 shows the $\chi^2$-square values for each row which correspond to a 1:1 segregation of altered flower phenotype to normal-flower phenotype.

TABLE 1

Segregation of Flower Type and Flower Color in $F_1$ Progeny

| Petal color of the normal flowering crossing partner | # of Normal Flowering Plants | | | | # of Altered Flowering Plants | | | | Total # of Plants | | | | $\chi^2$ Values Corresponding to a 1:1 segregation for flower type |
|---|---|---|---|---|---|---|---|---|---|---|---|---|---|
| | White | Pink | Purple | Total | White | Pink | Purple | Total | White | Pink | Purple | Total | |
| White | 174 | 23 | 41 | 238 | 46 | 5 | 44 | 95 | 220 | 28 | 85 | 333 | *61.4 |
| Purple | 3 | 8 | 263 | 274 | 3 | 3 | 68 | 74 | 6 | 11 | 331 | 348 | *114.8 |
| Pink | 3 | 217 | 33 | 253 | 1 | 7 | 6 | 14 | 4 | 224 | 39 | 267 | *213.94 |
| White | 59 | 28 | 35 | 122 | 23 | 7 | 21 | 51 | 82 | 35 | 56 | 173 | *29.14 |
| White-purple bicolored | 16 | 12 | 0 | 28 | 3 | 12 | 0 | 15 | 19 | 24 | 0 | 43 | *3.94 |
| Purple | 0 | 9 | 61 | 70 | 0 | 2 | 9 | 11 | 0 | 11 | 70 | 81 | *42.98 |
| Pink | 57 | 59 | 24 | 140 | 5 | 15 | 3 | 23 | 62 | 74 | 27 | 163 | *83.98 |
| Pink | 6 | 47 | 41 | 94 | 0 | 8 | 7 | 15 | 6 | 55 | 48 | 109 | *57.26 |
| Ivory | 110 | 0 | 0 | 110 | 23 | 0 | 0 | 23 | 133 | 0 | 0 | 133 | *56.90 |

*Respective progeny deviate significantly from a 1:1 segregation at $\chi^2$ = 3.84

After sexual propagation by crossbreeding into different *Osteospermum* cultivars and breeding lines, stable altered flowering seedlings were found among the $F_1$ progeny. The successful transmission of the altered flower trait into sexual progeny shows that this trait is genetically stable. However, the segregation pattern of the altered flower trait in different $F_1$ progeny does not explain the mode of inheritance of this mutation.

To further investigate the segregation pattern of the mutation leading to the altered flowering *Osteospermum* phenotype, four stable altered flowering genotypes were crossed with four normal flowering *Osteospermum* genotypes and five altered flowering genotypes were crossed among each other. The breeding parents were again selected according to their genetic distance based on the analysis of Gawenda and Debener (Gawenda, I. and Debener, T., Genetic diversity of *Osteospermum* genotypes analysed by AFLP and chloroplast SSR markers, *Europ. J. Hort. Sci.,* 74 (2), 86-94 (2009)). Since the altered flowering seedlings were not chimeric anymore, the segregation ratio in their offspring for normal-flowering genotypes should correspond to a 1:1 ratio as in the case of dominant inheritance. Pollination, seed harvest, and sowing as well as cultivation of the seedlings were performed as described above for the $F_1$ progeny. The progeny were evaluated for their flower types. Results showed that all progeny arising from a cross of an altered and a normal flowering parent correspond to a segregation ratio of 1:1. In case of progeny from crosses of two altered flowering parents three out of four populations corresponded to a segregation ratio of 3:1. These ratios observed in this analysis confirm a monogenic dominance inheritance of the mutation responsible for the altered flowering *Osteospermum* phenotype.

In the upper half of Table 2, column 1 shows the number of plants having the altered flowering phenotype resulting from crosses between an altered flowering $F_1$ plant with a normal flower plant, while column 2 shows the number of plants having the normal flowering phenotype and column 3 shows the total number of plants resulting from the crosses. Column 4 shows the $\chi^2$ square values corresponding to the expected 1:1 segregation of altered flowering phenotypes to normal flowering phenotypes for each row. In the lower half of Table 2, the same analysis was performed for crosses between two plants having the altered flowering phenotype.

TABLE 2

Segregation of the Altered Flower Type in $F_2$ Progeny

Crosses between altered flowering $F_1$ plants and normal-flowering plants

| Population code | # of Altered flowering plants | # of Normal flowering plants | Total # of Plants | $\chi^2$ Values corresponding to a 1:1 segregation pattern |
|---|---|---|---|---|
| 468 | 64 | 54 | 118 | 0.84 |
| 469 | 65 | 89 | 154 | 3.74 |
| 471 | 83 | 90 | 173 | 0.28 |
| 499 | 52 | 41 | 93 | 1.30 |
| 501 | 48 | 44 | 92 | 0.18 |
| 503 | 35 | 45 | 80 | 1.25 |
| 504 | 74 | 72 | 146 | 0.16 |
| 506 | 38 | 44 | 82 | 0.44 |
| 511 | 107 | 96 | 203 | 0.58 |
| 476 | 46 | 43 | 89 | 0.10 |

Crosses between two altered flower-type $F_1$ plants

| Population code | # of Altered flowering plants | # of Normal flowering plants | Total # of Plants | $\chi^2$ Values corresponding to a 3:1 segregation pattern |
|---|---|---|---|---|
| 8 | 129 | 44 | 173 | 0.01 |
| 9 | 66 | 18 | 84 | 0.84 |
| 3 | 15 | 52 | 67 | 0.24 |

* Respective combinations deviate significantly from the expected 3:1 segregation at $\chi^2$ = 3.84

Example 2

Molecular Marker Analysis of Flower Type in *Osteospermum*: Identification of an AFLP Marker Linked to the KLEDF Allele The aim of this project was the identification of markers linked to the altered flowering trait in *Osteospermum* by using a Bulked Segregant Analysis (BSA) approach. The markers were identified by using BSA in which proprietary F2 populations 511, 499 and 503 derived from a cross between an altered flowering *Osteospermum* parent and a normal flowering *Osteospermum* parent (Table 2) were used to detect the DNA markers linked to the locus controlling the altered flower phenotype. AFLP marker screening was carried out on these populations including their parents (n=279).

DNA Extraction and AFLP Analysis:

Genomic DNA was isolated from the leaf material using a modified CTAB protocol (Stewart and Via (1993) *Biotechniques* 14(5): 748-750). The AFLP analysis was conducted according to the standard protocol described by Vos et al. (1995) *Nucl. Acids Res.* 23:4407-4414 with the following details:

```
EcoRI adapter:
                                    (SEQ ID NO: 6)
5'-CTCGTAGACTGCGTACC (as 5' to 3' = SEQ ID NO: 7)
3'-CATCTGACGCATGGTTAA EcoRI adapter oligonucleotides:
                                    (SEQ ID NO: 6)
5'-CTCGTAGACTGCGTACC-3'

(SEQ ID NO: 7)
5'-AATTGGTACGCAGTCTAC-3'

MseI adapter:
                                    (SEQ ID NO: 8)
5'-GACGATGAGTCCTGAG (as 5' to 3' = SEQ ID NO: 9)
3'-TACTCAGGACTCAT MseI adapter oligonucleotides:
                                    (SEQ ID NO: 8)
5'-GACGATGAGTCCTGAG-3'

(SEQ ID NO: 9)
5'-TACTCAGGACTCAT-3'

Pre-amplification primers:
                                    (SEQ ID NO: 10)
E01L:     5'-AGACTGCGTACCAATTCA-3'

(SEQ ID NO: 11)
M02:      5'-GATGAGTCCTGAGTAAC-3'

Final AFLP PCR oligos:
                                    (SEQ ID NO: 1)
E40:      5'-GACTGCGTACCAATTCAGC-3'

(SEQ ID NO: 2)
M54:      5'-GATGAGTCCTGAGTAACCT-3'
```

Figure 15:
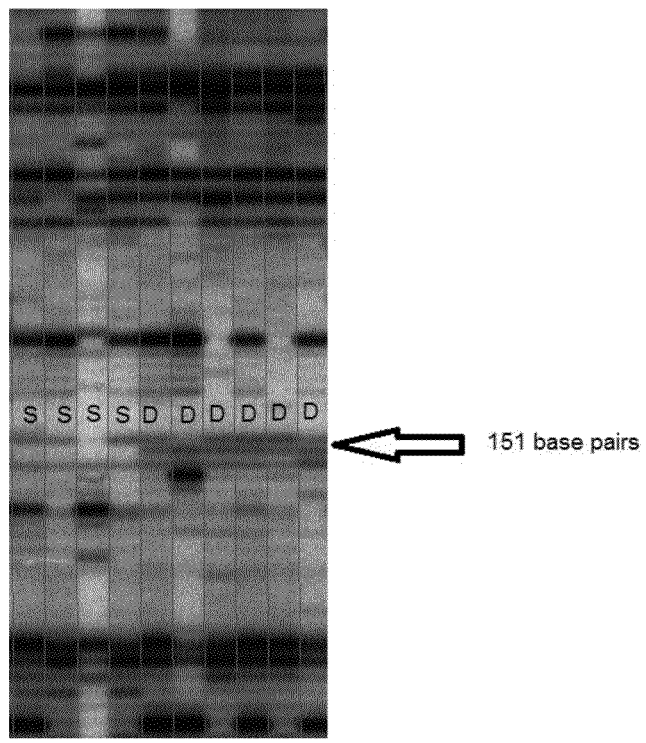
FIG. 15 shows the AFLP analysis of normal flowering *Osteospermum* plants (lanes 1-4) and altered flowering *Osteospermum* plants (lanes 5-10). The marker band of 151 bp, which is only present in the altered flowering plants of the present invention, is marked with an arrow.

Results:

An AFLP marker was found (E40/M54-151) which could clearly discriminate between the normal and altered flowering phenotype in *Osteospermum*. After separation on denaturing polyacrylamide gel this marker showed a band of size approximately 151 base pairs in altered flowering individuals, which was absent in all normal flowering ones (see FIG. 15). This AFLP marker therefore could immediately be used in breeding for identifying genotypes having an altered flowering phenotype.

Example 3

Molecular Marker Analysis of Flower Type in *Osteospermum*: Identification of SNP Marker Linked to the KLEDF Allele To identify molecular markers linked to the altered flowering phenotype in *Osteospermum* a candidate gene (CG) approach was used as an alternative to the AFLP marker approach. The working hypothesis assumed that single nucleotide polymorphisms (SNP) or insertion/deletions (Indel) within the candidate gene sequence are associated with the phenotype of interest. To our knowledge there has been no study involving genes responsible for alteration of floral morphology in *Osteospermum*. Among other members of Asteraceae such as sunflower and Gerbera phenotypes showing altered floral morphology have been reported. Several important genes which are assumed to be involved in change of floral morphology have been reported (Kotilainen et al. (2000) *Plant Cell* 12: 1893-1902; Theißen (2001) *Current Opinion in Plant Biology* 4: 75-85; Teeri et al. (2002) In: Cronck Q C B, Bateman R M, Hawkins J A, eds. Developmental genetics and plant evolution. London: Taylor & Francis, 220-232; Fambrini et al. (2003) *Genesis* 36: 25-33; Uimari et al. (2004) *Proc. Natl. Acad. Sci. USA* 101: 15817-15822; Broholm et al. (2008) *Proc. Natl. Acad. Sci. USA* 105: 9117-9122). From these studies we chose the genes GAGA1, CYCLODEA and GRCD2 as possible candidates causing floral morphology change in *Osteospermum*.

Since there has been no report on these genes being studied in *Osteospermum*, Gerbera sequences for these three genes were used for designing primers for *Osteospermum* homologs of these genes. Genomic DNA was extracted from the leaf material by using a standard extraction protocol. At the end of this experiment only one gene (CYCLODEA) homolog in *Osteospermum* could successfully be amplified and sequenced. In this fragment (approximately 330 bp long) a SNP (nucleotide T for normal to C for altered flowering plant) was identified which shows a strong linkage with the altered flowering *Osteospermum* genotypes.

Primer Sequence and PCR Conditions:

```
Forward primer:
                                              (SEQ ID NO: 3)
CYC2f6       5'-AAGATCGACACAGCTCACGG-3'

Reverse primer:
                                              (SEQ ID NO: 4)
CYC2r7       5'-TCTGCCCTTGACTGATTCAC-3'
```

Polymerase chain reaction amplifications were performed in 25 µL reaction volumes consisting of 2 µl (25-30 ng/µl) genomic DNA, 5 µl 5×GoTaq-buffer, 1.5 µl dNTPs (25 µM), 0.5 µl primer forward (10 µM), 0.5 µl primer r (10 µM), 0.2 µl GoTaq (5 U/µl), and 15.3 µl H$_2$O. The amplification protocol consisted of 35 cycles with an initial denaturing step of 5 min at 94° C. followed by 34 cycles at 94° C. for 1 min for denaturation, followed by primer-specific annealing 60° C. for 1 min and extension at 72° C. for 2 min. After 35 cycles, there was a final extension step of 10 min at 72° C.

Analysis of the Polymorphism in CYC2:

All sequence data for individuals involved in the analysis were assembled, edited and prepared for SNP screening. In the gene CYC2 sequence fragment we found a SNP with nucleotide base C which is tightly linked to the altered flowering phenotype. In the normal flowering individuals, there is a T at this position. The SNP position is shown below in Table 3.

TABLE 3

SNP position within the sequence
TTTGANAAAG (SEQ ID NO: 10)

| Flower type | Adjacent bases 5' of the SNP | SNP | Adjacent bases 3' of the SNP |
|---|---|---|---|
| Normal | TTTGA | T | AAAG |
| Altered | TTTGA | C | AAAG |

Example: Below a sequence alignment of the CYC2 gene fragment of a normal *Osteospermum* flowering plant (SEQ ID NO: 11) with that of an altered flowering plant (SEQ ID NO: 5) is shown and the position of the SNP is indicated in bold letters. The sequence alignment was performed using the EMBOSS Pairwise Alignment Algorithms available on the world wide web at: ebi.ac.uk/Tools/emboss/align/.

```
Normal    1  NNNGCNNGCTCG-GTCNNNCGGNNTAGNCGTGCANGGGCGNGNNTNTTCA   49
             ||  |||•| |•|    ||   ||• |||||  |||||| |  | ||••
Altered   1  TNNGC-TGCTNGTGCCG---GGAATANNCGTGC-NGGGCGNGNNTNTTTC  45

Normal   50  AGGGCAGAAG-ATTTGCTAGGGTTTGATAAAG-CTNGCAAAACCCTTGAT   97
             ||||||||||  |||||||||||||||||•||||•|  ||||||||||||
Altered  46  AGGGCAGAAGCATTTGCTAGGGTTTGACAAAGTNTTGCAAAACCCTTGAT   95

Normal   98  TGGCTCTTTACCAAGTCCAAGACCGCAATTAAGGAGTTGGTTGAAGAAAT  147
             ||||||||||||||||||||||||||||||||||||||||||||||||||
Altered  96  TGGCTCTTTACCAAGTCCAAGACCGCAATTAAGGAGTTGGTTGAAGAAAT  145

Normal  148  GAAACACAGTTCATCTTCTGGTGCTACTGATCAATGTGAGGTTTTTCAGG  197
             ||||||||||||||||||||||||||||||||||||||||||||||||||
Altered 146  GAAACACAGTTCATCTTCTGGTGCTACTGATCAATGTGAGGTTTTTCAGG  195

Normal  198  AGACCATCATGAGGATATCAAATGAAAAAGATAAAGGCGAAAAGAAGAAG  247
             ||||||||||||||||||||||||||||||||||||||||||||||||||
Altered 196  AGACCATCATGAGGATATCAAATGAAAAAGATAAAGGCGAAAAGAAGAAG  245

Normal  248  TCAGTACCCAATGTTCTTGAAGGAAAAAAGAAAAAAACTGCCCGAAAATA  297
             ||||||||||||||||||||||||||||||||||||||||||||||||||
Altered 246  TCAGTACCCAATGTTCTTGAAGGAAAAAAGAAAAAAACTGCCCGAAAATA  295

Normal  298  TAAATCTGGAGTCGATGTGAATCAGTCAAGGGC    -330  (SEQ ID NO: 11)
             |||||||||||||||||||||||||||||||||
Altered 296  TAAATCTGGAGTCGATGTGAATCAGTCAAGGGCAG  -330  (SEQ ID NO: 5)
```

This result was confirmed for population 511 as well as for population 503 and for other individuals involved in this study. This SNP marker could thus immediately be used in breeding for identifying genotypes having altered flowering phenotype.

Example 4

Further Characterization of the Altered Flowering Plants

The altered flowering trait was crossbred into different genetic backgrounds representing the available range of growing habits and flower colors in *Osteospermum*. The segregation of plant characteristics like flower color, flower size, earliness, branching, vigor, and foliage quality in the offspring was according to the segregation patterns in normal-flowering offspring. Surprisingly, these plant characteristics do not seem to be linked to the altered flowering trait, as is also indicated by the results presented in Table 4. Furthermore, all individuals which were selected from the different progeny and analysed further performed similarly to typical-flowering *Osteospermum* plants in terms of rooting, cutting production, growing habit and disease/pest resistance.

Table 4 column 1 shows the code for each line, column 2 shows whether the line has the altered flowering phenotype (AF) or the normal-flowering phenotype (NF), columns 3 through 6 show the number of ray florets, the length and width in centimeters of the ray florets and the upper surface colors of the ray florets, respectively. For those plants, which are bicolored or exhibit playing or fading colors, more than one RHS number according to the color chart available from the Royal Horticultural Society (available on the world wide web at rhs.org.uk/Plants/RHS-Publications/RHS-color-charts)) is listed. Columns 7 through 9 show the number of disc florets and the length in centimeters of the disc florets as well as the average length, columns 10 and 11 show the length and width in centimeters of the immature leaves, columns 12 and 13 show the length and width in centimeters of the mature foliage, column 14 shows the color of the mature foliage, and column 15 shows the number of basal shoots for each line.

TABLE 4

Comparison of Certain Plant Characteristics between Normal- and Altered Flowering Osteospermum Genotypes

| | | Ray florets | | | | Disc florets | | Average |
|---|---|---|---|---|---|---|---|---|
| Code | Type | No. | Length | Width | Color (RHS) | No. | Length | Length |
| OE 2008248 | AF | 14-16 | 3.0 | 0.7 | 92D | 80-85 | 1.3-2.1 | 1.7 |
| OE 2008258 | AF | 17-18 | 2.6-2.7 | 0.7-0.8 | 92D | 73-89 | 1.0-1.9 | 1.45 |
| OE 2008274 | AF | 25 | 2.6-2.9 | 0.7-0.9 | 78B | 95-96 | 1.3-1.7 | 1.5 |
| OE 2008285 | AF | 22-25 | 2.6-3.0 | 0.6-0.8 | N74B | 78-85 | 0.8-2.2 | 1.5 |
| OE 2008384 | AF | 23-27 | 2.1 | 0.6-0.7 | 72A | 94-108 | 1.4-1.7 | 1.55 |
| OE 2008390 | AF | 19-22 | 2.6 | 0.8-0.9 | 77C + 75D | 68-100 | 1.4-1.8 | 1.6 |
| A-5-43 | NF | 17-20 | 3.2-3.3 | 1.0 | 155D | 65-90 | 0.5-0.6 | 0.55 |
| V 78 | NF | 19-22 | 3.3-3.4 | 1.1-1.2 | 155D | 81-89 | 0.4-0.6 | 0.5 |
| W 113 | NF | 18-21 | 2.4-2.9 | 0.7-0.9 | 157C | 40-45 | 0.4-0.5 | 0.45 |
| A-48-24 | NF | 20-23 | 2.6 | 0.6-0.8 | 71A/N81A | 77-96 | 0.5-0.6 | 0.55 |
| X 95 | NF | 23-25 | 3.4-3.7 | 0.9 | N78A/83 | 65-79 | 0.5-0.6 | 0.55 |
| A-69-1 | NF | 21-25 | 2.7 | 0.8 | 72A/N78A | 93-107 | 0.6 | 0.6 |
| V 34 | NF | 19-20 | 2.6-2.8 | 0.8-0.9 | 70B/N82A | 72-81 | 0.4-0.5 | 0.45 |
| W 42 | NF | 16-20 | 2.4-2.6 | 0.7 | 78B/78C/80C | 58-75 | 0.5-0.6 | 0.55 |
| A-46-1 | NF | 19-20 | | | N74C + 155D/N82B | 63-70 | 0.5 | 0.5 |

| | | Foliage -Immature | | | Foliage - Mature | | | No. basal |
|---|---|---|---|---|---|---|---|---|
| Code | Type | No. | Length | Width | Length | Width | Color (RHS) | shoots |
| OE 2008248 | AF | 14-16 | 3.5 | 0.9 | 4.8-5.0 | 1.6-1.9 | 146A | 6 |
| OE 2008258 | AF | 17-18 | 3.2 | 0.8 | 5.2 | 1.9-2.0 | 144A | 5 |
| OE 2008274 | AF | 25 | 3.2 | 0.8-0.9 | 4.5-4.9 | 2.0 | 146A | 5 |
| OE 2008285 | AF | 22-25 | 4.0-4.5 | 1.2-1.6 | 7.0-7.5 | 2.5-3.5 | 137A | 5 |
| OE 2008384 | AF | 23-27 | 3.4 | 1.1 | 4.1 | 2.1 | 146A | 4 |
| OE 2008390 | AF | 19-22 | 3.3 | 0.9-1.1 | 6.5 | 2.0-2.5 | 146A | 5 |
| A-5-43 | NF | 17-20 | 3.3-3.9 | 1.0-1.2 | 6.0-7.0 | 2.3-2.5 | 146A | 4 |
| V 78 | NF | 19-22 | 3.5-4.0 | 0.9-1.2 | 6.2-7.3 | 2.1-2.4 | N137B | 5 |
| W 113 | NF | 18-21 | 3.2-3.6 | 0.8-1.0 | 5.5-6.0 | 1.6-1.8 | 146A | 6 |
| A-48-24 | NF | 20-23 | 2.4-2.9 | 0.8-10. | 5.5-6.5 | 2.0-3.0 | 146A | 4 |
| X 95 | NF | 23-25 | 3.1-3.5 | 1.0-1.1 | 5.9-6.4 | 2.5 | 147A | 4 |
| A-69-1 | NF | 21-25 | 2.8 | 0.7-1.1 | 6.3-6.6 | 2.5 | 147A | 4 |
| V 34 | NF | 19-20 | 2.5-2.7 | 0.6 | 6.1-6.4 | 2.6 | N137B | 5 |
| W 42 | NF | 16-20 | 2.8 | 0.9-1.0 | 4.3-4.6 | 1.6-1.8 | 146A | 5 |
| A-46-1 | NF | 19-20 | 2.3-2.8 | 0.7-0.8 | 5.8-6.3 | 2.5-2.7 | 147A | 4 |

By the described method 6 genotypes were developed which stably exhibit the new altered flower phenotype (see FIG. 7 through FIG. 12). Table 4 summarizes the comparison of certain plant characteristics in these altered flowering genotypes compared to normal-flowering *Osteospermum* plants. As shown in Table 4, unexpectedly, the altered flowering group consistently differs from the normal-flowering ones in the length of the disc florets, whereas all further plant characteristics show the same variation in the altered flowering genotypes as in the normal-flowering ones.

From the progeny described previously, 10 altered flowering *Osteospermum* genotypes were selected and evaluated under different environmental conditions in North and South Europe, East Africa, and the United States covering a broad temperature range and different light regimes. The plants were grown in the greenhouse as well as in the field. The altered flowering trait was always expressed, whereas the expression level as well as the expression of the different phenotypes described above varied depending on the growing conditions. These observations indicate that the mutant KLEDF allele of the present invention is genetically stable.

Example 5

Genotype OE 2008 248

Through the breeding process described above, *Osteospermum* genotype OE 2008 248 was developed. OE 2008 248 displays the altered flower phenotype of the present invention having enlarged disc florets.

TABLE 5

PHENOTYPIC DESCRIPTION OF THE GENOTYPE OE 2008 248

PLANT:

Ploidy level: 4x
Number of basal shoots: 6
Internode length: 0.05 cm to 1.0 cm
FOLIAGE:
Immature leaves:

Length: 3.5 cm
Width: 0.9 cm
Mature leaves:

Length: 4.8 cm to 5.0 cm
Width: 1.6 cm to 1.9 cm
Color: RHS 146A
RAY FLORETS:

Number: 14 to 16
Length: 3.0 cm
Width: 0.7 cm
Color of upper surface: RHS 92D
Color of lower surface: RHS 85A
DISC FLORETS:

Number: 80 to 85
Length: 1.3 cm to 2.1 cm
Average length: 1.7 cm
Color of inner surface: RHS 85D
Color of outer surface: RHS 91A

Example 6

Genotype OE 2008 258

Through the breeding process described above, *Osteospermum* genotype OE 2008 258 was developed. OE 2008 258 displays the altered flower phenotype of the present invention having enlarged disc floret corollas.

TABLE 6

PHENOTYPIC DESCRIPTION OF THE GENOTYPE OE 2008 258

PLANT:

Ploidy level: 4x
Number of basal shoots: 5
Internode length: 0.5 cm to 1.0 cm
FOLIAGE:
Immature leaves:

Length: 3.2 cm
Width: 0.8 cm

TABLE 6-continued

PHENOTYPIC DESCRIPTION OF THE GENOTYPE OE 2008 258

Mature leaves:

Length: 5.2 cm
Width: 1.9 cm to 2.0 cm
Color: RHS 144A
RAY FLORETS:

Number: 17 to 18
Length: 2.6 cm to 2.7 cm
Width: 0.7 cm to 0.8 cm
Color of upper surface: RHS 92D
Color of lower surface: RHS 76A
DISC FLORETS:

Number: 73 to 89
Length: 1.0 cm to 1.9 cm
Average length: 1.45 cm
Color of inner surface: RHS 85D
Color of outer surface: RHS 76C

Example 7

Genotype OE 2008 274

Through the breeding process described above, *Osteospermum* genotype OE 2008 274 was developed. OE 2008 274 displays the altered flower phenotype of the present invention having enlarged disc floret corollas.

TABLE 7

PHENOTYPIC DESCRIPTION OF THE GENOTYPE OE 2008 274

PLANT:

Ploidy level: 4x
Number of basal shoots: 5
Internode length: 0.5 cm to 1.0 cm
FOLIAGE:
Immature leaves:

Length: 3.2 cm
Width: 0.8 cm to 0.9 cm
Mature leaves:

Length: 4.5 cm to 4.9 cm
Width: 2.0 cm
Color: RHS 146A
RAY FLORETS:

Number: 25
Length: 2.6 cm to 2.9 cm
Width: 0.7 cm to 0.9 cm
Color of upper surface: RHS 78B
Color of lower surface: RHS 82A
DISC FLORETS:

Number: 95 to 96
Length: 1.3 cm to 1.7 cm
Average length: 1.5 cm
Color of inner surface: RHS 78A
Color of outer surface: RHS 82D

Example 8

Genotype OE 2008 285

Through the breeding process described above, *Osteospermum* genotype OE 2008 285 was developed. OE 2008 285 displays the altered flower phenotype of the present invention having enlarged disc florets.

TABLE 8

PHENOTYPIC DESCRIPTION OF
THE GENOTYPE OE 2008 285

PLANT:

Ploidy level: 4x
Number of basal shoots: 5
Internode length: 0.5 cm to 1.0 cm
FOLIAGE:
Immature leaves:

Length: 4.0 cm to 4.5 cm
Width: 1.2 cm to 1.6 cm
Mature leaves:

Length: 7.0 cm to 7.5 cm
Width: 2.5 cm to 3.5 cm
Color: RHS 137A
RAY FLORETS:

Number: 22 to 25
Length: 2.6 cm to 3.0 cm
Width: 0.6 cm to 0.8 cm
Color of upper surface: RHS N74B
Color of lower surface: RHS 84A
DISC FLORETS:

Number: 78 to 85
Length: 0.8 cm to 2.2 cm
Average length: 1.5 cm
Color of inner surface: RHS 72A
Color of outer surface: RHS 84A

Example 9

Genotype OE 2008 384

Through the breeding process described above, *Osteospermum* genotype OE 2008 384 was developed. OE 2008 384 displays the altered flower phenotype of the present invention having enlarged disc floret corollas.

TABLE 9

PHENOTYPIC DESCRIPTION OF
THE GENOTYPE OE 2008 384

PLANT:

Ploidy level: 4x
Number of basal shoots: 4
Internode length: 0.5 cm to 1.0 cm
FOLIAGE:
Immature leaves:

Length: 3.4 cm
Width: 1.1 cm
Mature leaves:

Length: 4.1 cm
Width: 2.1 cm
Color of upper surface: RHS 146A
RAY FLORETS:

Number: 23 to 27
Length: 2.1 cm
Width: 0.6 cm to 0.7 cm
Color of upper surface: RHS 72A
Color of lower surface: RHS N80D

TABLE 9-continued

PHENOTYPIC DESCRIPTION OF
THE GENOTYPE OE 2008 384

DISC FLORETS:

Number: 94 to 108
Length: 1.4 cm to 1.7 cm
Average length: 1.55 cm
Color of inner surface: RHS 72A
Color of outer surface: RHS 84B

Example 10

Genotype OE 2008 390

Through the breeding process described above, *Osteospermum* genotype OE 2008 390 was developed. OE 2008 390 displays the altered flower phenotype of the present invention having enlarged disc floret corollas.

TABLE 10

PHENOTYPIC DESCRIPTION OF
THE GENOTYPE OE 2008 390

PLANT:

Ploidy level: 4x
Number of basal shoots: 5
Internode length: 0.5 cm to 1.0 cm
FOLIAGE:
Immature leaves:

Length: 3.3 cm
Width: 0.9 cm to 1.1 cm
Mature leaves:

Length: 6.5 cm
Width: 2.0 cm to 2.5 cm
Color of upper surface: RHS 146A
RAY FLORETS:

Number: 19 to 22
Length: 2.6 cm
Width: 0.8 cm to 0.9 cm
Color of upper surface: RHS 77c and RHS 75D
Color of lower surface: RHS 85A
DISC FLORETS:

Number: 68 to 100
Length: 1.4 cm to 1.8 cm
Average length: 1.6 cm
Color of inner surface: RHS 77C
Color of outer surface: RHS 85A

Example 11

Incorporating the Mutant Allele KLEDF into *Osteospermum* Plants

The altered flowering cultivars having the mutant allele named KLEDF of the present invention maintain functional female and male organs. Therefore, the altered flowering trait can be incorporated into *Osteospermum* cultivars through conventional breeding, although the execution/implementation of these crosses requires specific skills of the respective pollinators. By crossbreeding, the KLEDF allele of the present invention can be incorporated into a broad range of *Osteospermum* plants having different flower colors and shapes (e.g., spider types) as well as into different foliage types. Furthermore, the mutant allele can be incorporated into plants having different growing habits, e.g., prostrate or hanging types can be developed besides erect or semi-erect types.

Using conventional breeding methods, an altered flowering Osteospermum plant having the mutant allele KLEDF of the present invention is crossed with a normal flowering Osteospermum plant lacking the mutant allele of the present invention. The resulting seeds are sown and the seedlings are grown according to conventional methods. The flowering $F_1$ progeny are then scored for altered flowering plants. Selected $F_1$ plants are further crossbred or can be crossed back to their altered flowering or to their normal-flowering parent in order to combine the altered flowering phenotype with further desirable plant characteristics. However, depending on the genetic distance between the parents, inbreeding-depression might occur in this backcross progeny. Alternatively, selected plants from this $F_1$ progeny can be outcrossed to selected plants from a different $F_1$ progeny or to another cultivar, which is far related to the respective $F_1$ progeny.

Example 12

Incorporating the Mutant Allele KLEDF into other Osteospermum Species to Create Interspecific Hybrids The mutant allele KLEDF of the present invention can be introduced into an interspecific hybrid made between one species of Osteospermum having the mutant allele of the present invention and a different Osteospermum species. A selected Osteospermum plant having the mutant allele KLEDF is crossed, using conventional methods, as either a male or a female parent, to a selected genotype of any further Osteospermum species. Depending on the Osteospermum species from which the crossing parent is selected, seeds will set easily, e.g., in crossings with O. jucundum. For crosses with plants from less closely related species, specific techniques like bud pollination, removal of the stigma and pollination of the remaining style, $GA_3$-treatments of the pollinated stigmas, and/or embryo rescue of the immature embryo may be necessary. The seeds resulting from the cross are sown and the seedlings are grown according to conventional methods. The flowering $F_1$ progeny are then scored for altered flowering plants. The further breeding procedure is similar to the procedure described in Example 11.

Example 13

Incorporating the Mutant Allele KLEDF into Dimorphoteca Plants to Create Intergeneric Hybrids Furthermore, the mutant KLEDF allele of the present invention can also be introduced into an intergeneric hybrid through crosses between a selected Osteospermum plant having the mutant allele KLEDF of the present invention and a Dimorphoteca plant lacking the mutant allele of the present invention. The methods to be used to realize these hybrids correspond to the methods which have been described for interspecific crosses, meaning that specific techniques like bud pollination, removal of the stigma and pollination of the remaining style, $GA_3$-treatments of the pollinated stigmas, and/or embryo rescue of the immature embryo may be necessary to realize these hybrid seedlings.

Example 14

Creating Plants of the Present Invention with the Assistance of Molecular Markers The incorporation of the mutant allele KLEDF of the present invention into a different genetic background requires repeated crossbreeding or backcrossing, meaning that the gene of interest has to be followed over several generations in the respective progeny. Molecular markers are a very powerful tool to make the selection more efficient and to accelerate the breeding process. Debener (Debener, T., Molecular markers as a tool for analysis of genetic relatedness and selection in ornamentals, *Breeding for Ornamentals: Classical and Molecular Approaches,* 329-345, Kluwer Academic Publishers (2002)) have described several examples of successful marker-assisted breeding in ornamentals.

We have found one AFLP and one SNP marker which clearly identify altered flowering genotypes. This is of particular importance to accelerate a breeding program through marker-assisted selection when identification of genotypes having an altered flowering phenotype is required at an early stage.

The application of these techniques will enable molecular mapping of the described Osteospermum KLEDF mutant allele of the present invention.

Example 15

Creating Plants of the Present Invention Using Protoplast Fusion

In some plant species protoplast fusion is a powerful technique to combine the genes of two different species instead of performing crosses between plants of the respective species (Horita, M., Morohashi, H., and Komai, F., Production of fertile somatic hybrid plants between oriental hybrid lily and Lilium×formolongi, *Planta,* 597-601 (2003); Griesbach, R. J., Recent advances in the protoplast biology of flower crops, *Scientia Horticulturae,* 37, 247-256 (1988); Kumar, A. and Cocking, E. C., Protoplast Fusion: A Novel Approach to Organelle Genetics in Higher Plants, *American Journal of Botany,* 741, 1289-1303 (1987)). Besides the addition of two complete genomes, parts of both genomes can be combined. Prerequisite is an efficient protocol for the regeneration of plants from single protoplasts. Even the transmission of just single chromosomes of one partner into the genome of the second partner or the incorporation of the genome of one partner into the cytoplasm of the second partner, as well as a patch-work cytoplasm can be achieved through protoplast fusion (see, for example, Lössl A., Adler, N., Horn, R., Frei, U., and Wenzel, G., Chondriome-type characterization of potato: Mtα, β, γ, δ, ε and novel plastid mitochondrial configurations in somatic hybrids, *Theoretical and Applied Genetics,* 99: 1-10 (1999)).

Protoplast fusion has been described in the genus Dimorphoteca (J. S. Al-Atabee, and J. B. Power (1987) *Plant Cell Reports* 6:414-416). However, since plants of both the Osteospermum and the Dimorphoteca genus are routinely propagated in tissue culture and can easily be regenerated from leaf explants, protoplast regeneration, as well as protoplast fusion might as well be possible in the genus Osteospermum (Allavena, A. et al. (2000) *Acta Hort.* 508: 129-133; Giovannini, A. et al. (1999) *In Vitro Cell. Dev. Biol. Plant* 35: 70-75). Fusion of protoplasts from an Osteospermum plant having the mutant allele KLEDF of the present invention with protoplasts from either an Osteospermum or a Dimorphoteca plant lacking the mutant allele of the present invention, regeneration of plants thereof, and selection of altered flower individuals among these regenerated fusion products, enable the transmission of the mutant allele of the present invention into new genetic backgrounds.

Example 16

Using Mutagens on Plants of the Present Invention to Create Altered Plants

Osteospermum and Dimorphoteca plants having the mutant allele KLEDF of the present invention can be used to induce further mutations, leading to further altered flower shapes or new flower colors, altered growing habits, foliage characteristics, etc. Mutants may appear spontaneously or mutations can be induced with Gamma irradiation or through treatment with certain chemical agents like ethyl methanesulfonate (EMS) (Broertjes, C. and van Harten, A. M., Applied mutation breeding for vegetatively propagated crops, *Developments in Crop Science* 12, Elsevier Science Publishers B.V. (1988)). Whereas these treatments mainly induce point mutations or chromosome mutations, genome mutations such as doubling of chromosome numbers can be produced, e.g., by treatment with colchicine. Even tissue culture can induce mutations, which are generally described as somaclonal variation (Chen, W. H., Chen, T. M., Fu, Y. M., and Hsieh, R. M., Studies on somaclonal variation in *Phalaenopsis, Plant Cell Rep*, 18, 7-13 (1998)).

Example 17

Using Transformation on the Plants of the Present Invention

Within the past decades genetic transformation has been a very powerful technique to transfer single genes from one plant into another regardless of crossing barriers. Besides genes for single structural proteins, which might modify flower color or induce specific biotic resistances, genes encoding transcription factors, which manipulate a broader range of complex plant characters, have been successfully transferred even between different plant families or organisms.

A protocol for genetic transformation of Osteospermum has been developed and several genes, including the marker gene β-glucuronidase as well as the rolB-gene, have been introduced into this plant species by *Agrobacterium tumefaciens*-mediated gene transfer. The following protocol has been developed, briefly: Leaf segments from Osteospermum tissue culture plants are incubated with a disarmed *Agrobacterium tumefaciens* strain which carries a vector with the gene of interest and a gene encoding a specific selectable marker, e.g., nptII for kanamycin selection. By regeneration under selection pressure according to the selectable marker, transgenic plants can be regenerated from single transformed cells (Allavena, A. et al. (2000) *Acta Hort*. 508: 129-133; Giovannini, A. et al. (1999) *In Vitro Cell. Dev. Biol. Plant* 35: 70-75).

The use of genetic transformation is imaginable for both directions: foreign genes can be transferred into an Osteospermum or a Dimorphoteca plant having the mutant allele KLEDF of the present invention and lead to a plant with completely new characteristics. Alternatively, the mutant KLEDF allele of the present invention or its respective cDNA can be transferred into foreign genetic backgrounds and induce altered flowers in the resulting transgenic plants.

Example 18

Incorporating the Mutant Allele KLEDF into Dimorphoteca Plants

Through intergeneric hybridization the mutant allele named KLEDF of the present invention can be introduced into the genus Dimorphoteca. Furthermore, the altered flowering trait can be incorporated into a broad range of Dimorphoteca cultivars through conventional breeding. By crossbreeding, the KLEDF allele of the present invention can be incorporated into Dimorphoteca cultivars having different flower colors and shapes as well as different foliage types. Furthermore, the mutant allele can be incorporated into plants having different growing habits, e.g., prostrate or hanging types can be developed besides erect or semi-erect types.

Using conventional breeding methods, a Dimorphoteca plant having the mutant allele KLEDF of the present invention is crossed with a Dimorphoteca plant lacking the mutant allele of the present invention. The resulting seeds are sown and the seedlings are grown according to conventional methods. The flowering $F_1$ progeny are then scored for altered flowering plants. Selected $F_1$ plants are further crossbred or they can be crossed back to their altered flowering or to their normal-flowering parent in order to combine the altered flowering phenotype with further desirable plant characteristics. However, depending on the genetic distance between the parents, inbreeding-depression might occur in this backcross progeny. Alternatively, selected plants from this $F_1$ progeny can be outcrossed to selected plants from a different $F_1$ progeny or to another cultivar, which is far related to the respective $F_1$ progeny.

Example 19

Incorporating the Mutant Allele KLEDF into Dimorphoteca Plants to Create Interspecific Hybrids The mutant allele KLEDF of the present invention can be introduced into an interspecific hybrid made between one species of Dimorphoteca having the mutant allele of the present invention and a different Dimorphoteca species. A selected Dimorphoteca plant having the mutant allele KLEDF is crossed, using conventional methods, as either a male or a female parent, to a selected genotype of any further Dimorphoteca species. For crosses with plants from less closely related species, specific techniques like bud pollination, removal of the stigma and pollination of the remaining style, $GA_3$-treatments of the pollinated stigmas, and/or embryo rescue of the immature embryo may be necessary. The seeds resulting from the cross are sown and the seedlings are grown according to conventional methods. The flowering $F_1$ progeny are then scored for altered flowering plants. Further breeding procedure is similar to the procedure described in Example 18. However, since the genus Dimorphoteca is representing species with different ploidy levels ranging from 2× to 6×, the resulting hybrids might for example be triploid and not produce viable seeds. Therefore, for further breeding the chromosome number of these plants must e.g. be doubled through treatment with colchicine.

Example 20

Incorporating the Mutant Allele KLEDF into Osteospermum Plants to Create Intergeneric Hybrids Furthermore, the mutant KLEDF allele of the present invention can also be introduced into an intergeneric hybrid through crosses between a selected Dimorphoteca plant having the mutant allele KLEDF of the present invention and an Osteospermum plant lacking the mutant allele of the present invention. The methods to be used to realize these hybrids correspond to the methods which have been described for interspecific crosses, meaning that specific techniques like bud pollination, removal of the stigma and pollination of the remaining style, $GA_3$-treatments of the pollinated stigmas, and/or embryo rescue of the immature embryo as well as chromosome doubling with colchicine may be necessary to realize these hybrid seedlings.

Example 21

Comparison of Seed Yield of Altered and Normal Flowering *Osteospermum* Genotypes During the course of altered flowering *Osteospermum* breeding work it was observed that normal flowering *Osteospermum* have a higher seed yield than altered flowering *Osteospermum*. To confirm this, ten normal and ten altered flowering *Osteospermum* genotypes were planted on the beds in open fields without any isolation barrier between them. Four plants per genotype were planted in one plot. Furthermore altered flowering *Osteospermum* genotypes were planted in isolation as well. Matured seeds were collected from each plant of each genotype and counted. It was observed that there was no difference in the seed yield between altered flowering *Osteospermum* planted alongside normal flowering types and those planted in isolation (mean seed yield/plant=21). However, the statistical analysis of the seed data clearly showed that under both conditions the altered flowering *Osteospermum* genotypes had significantly lower seed yields than normal flowering *Osteospermum* genotypes.

TABLE 11

Seed yields of the normal and altered *Osteospermum* genotypes

| Flower Type | N | Mean no. of seeds | Standard error of mean | t | Significance |
|---|---|---|---|---|---|
| Normal | 10 | 233.22 | 44.36 | 4.76 | 0.001 |
| Altered | 10 | 20.44 | 5.4 | | |

Example 22

Comparison of Flower Keepability of Altered and Normal Flowering *Osteospermum* Genotypes It was observed that altered flowering *Osteospermum* flowers have a longer keepability than normal flowering *Osteospermum* plants. In order to confirm this observation, we planted ten plants each of four normal and four altered flowering *Osteospermum* genotypes in the greenhouse (August-December 2010). The plants were not pinched and were thus allowed to grow and bear flower on the central stem. These flowers were regularly marked as i) opened: when the flower buds start showing the color of the petals and were marked as ii) wilted: when two-three petals started showing aged symptoms and flower started appearing dull. For each genotype the difference between the day flower opened and the day it wilted was taken as flower keepability.

TABLE 12

Comparison of flower keepability of the normal and altered flowering *Osteospermum* genotypes

| Flower Type | N | Mean (days) | t | Significance |
|---|---|---|---|---|
| Normal flowering | 4 | 11.98 | -2.575 | 0.05 |
| Altered flowering | 4 | 15.30 | | |

Example 23

Plant Growth Regulator Treatment of Altered Flowering *Osteospermum*

Spraying an altered flowering *Osteospermum* rooted cutting weekly with a 0.2% solution of plant growth regulator Daminozide (sold under brand name Alar) transformed altered flowering *Osteospermum* flowers back to phenotypically almost normal appearing flowers. On plants of an altered flowering *Osteospermum* which were sprayed this way sometimes a part of and sometimes all elongated disc florets disappeared, so that the disc florets resembled the disc florets on a normal flowering *Osteospermum* plant. In an altered flowering *Osteospermum* flower pollen is usually sparse which seriously limits the seed yield resulting from the crosses involving an altered flowering male parent. In contrast, flowers of a plant sprayed with Alar had almost comparable quantities of pollen as seen on a plant having normal type of flowers. This makes the crossing procedure convenient, as there is ample of pollen on plants with altered flowers which are genetically altered, but exhibit the normal type of flowers. Therefore, an altered flowering plant treated with Daminozide may easily and quickly be crossed with a normal flowering plant and with another altered flowering plant as well.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. All publications cited in this application are herein incorporated by reference.

Deposit Information

*Osteospermum* seeds containing the KLEDF mutant allele of this invention and capable of displaying the altered flower phenotype of the present invention have been placed on deposit under the Budapest Treaty with National Collections of Industrial, Food and Marine Bacteria (NCIMB), 23 St Machar Drive, Aberdeen, Scotland, AB24 3RY, United Kingdom under NCIMB Accession No. 41698. The date of deposit was Feb. 26, 2010.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. An *Osteospermum* plant having an altered flower phenotype, wherein at least one inflorescence has at least one disc floret with a length of at least 0.8 cm, wherein the *Osteospermum* plant comprises a DNA sequence, which upon amplification with the primers according to SEQ ID NOs: 3 and 4 yields a fragment comprising a sequence TTTGANAAAG (SEQ ID NO: 10) wherein N is C.

2. The *Osteospermum* plant of claim 1, wherein the length of the at least one disc floret is at least 1.3 cm.

3. The *Osteospermum* plant of claim 1, wherein the average length of the at least one disc floret is between 1.25 cm and 6 cm.

4. The *Osteospermum* plant of claim 1, wherein the ratio between the average length of the longest and the shortest ray floret of at least one inflorescence and the average length of the longest and the shortest disc floret of at least one inflorescence is less than 2.0.

5. An *Osteospermum* plant having an altered flower phenotype, wherein at least one inflorescence has at least one disc floret with a length of at least 0.8 cm, wherein the *Osteospermum* plant comprises a DNA sequence which after restriction digestion with EcoRI and MseI and annealing of the adapters according to SEQ ID NOs: 6 to 9 is a template for amplification of a DNA fragment of about 151 nucleotides with the primers according to SEQ ID NOs: 1 and 2.

6. A cell, seed or protoplast produced from the plant of claim 1 comprising said fragment, or a tissue culture of regenerable cells comprising said fragment produced from said plant, wherein said cells of the tissue culture are produced from a plant part selected from the group consisting of leaf, pollen, embryo, cotyledon, hypocotyl, meristematic cell, protoplast, root, root tip, pistil, anther, stem, petiole, ray floret, and disc floret.

7. An *Osteospermum* seed containing a mutant allele designated KLEDF, wherein a representative sample of seed containing said KLEDF allele has been deposited under NCIMB Accession No. 41698.

8. An *Osteospermum* plant, or a part thereof, produced by growing the seed of claim 7.

9. A cell, seed or protoplast produced from the plant of claim 8 comprising said mutant allele designated KLEDF, or a tissue culture of regenerable cells comprising said mutant allele designated KLEDF produced from said plant, where said cell, seed, protoplast or cells of the tissue culture are produced from a plant part selected from the group consisting of leaf, pollen, embryo, cotyledon, hypocotyl, meristematic cell, protoplast, root, root tip, pistil, anther, stem, petiole, ray floret, and disc floret.

10. An *Osteospermum* plant regenerated from said cell, seed, protoplast or tissue culture of claim 9.

11. A method of increasing seed yield in a plant according to claim 1, comprising treating the plant with a plant growth regulator.

12. The method of claim 11, wherein the plant growth regulator is daminozide.

13. The *Osteospermum* plant of claim 8, wherein the length of the at least one disc floret is at least 1.3 cm.

14. The *Osteospermum* plant of claim 8, wherein the average length of the at least one disc floret is between 1.25 cm and 6 cm.

15. The *Osteospermum* plant of claim 8, wherein the ratio between the average length of the longest and the shortest ray floret of at least one inflorescence and the average length of the longest and the shortest disc floret of at least one inflorescence is less than 2.0.

16. A cell, seed or protoplast produced from the plant of claim 5 capable of producing said DNA fragment of about 151 nucleotides, or a tissue culture of regenerable cells capable of producing said DNA fragment of about 151 nucleotides produced from said plant, wherein said cells of the tissue culture are produced from a plant part selected from the group consisting of leaf, pollen, embryo, cotyledon, hypocotyl, meristematic cell, protoplast, root, root tip, pistil, anther, stem, petiole, ray floret, and disc floret.

* * * * *

SEQUENCE LISTING

<160> NUMBER OF SEQ ID NOS: 11

<210> SEQ ID NO 1
<211> LENGTH: 19
<212> TYPE: DNA
<213> ORGANISM: artificial sequence
<220> FEATURE:
<223> OTHER INFORMATION: primer E40

<400> SEQUENCE: 1
gactgcgtac caattcagc                                                19

<210> SEQ ID NO 2
<211> LENGTH: 19
<212> TYPE: DNA
<213> ORGANISM: artificial
<220> FEATURE:
<223> OTHER INFORMATION: primer M54

<400> SEQUENCE: 2
gatgagtcct gagtaacct                                                19

<210> SEQ ID NO 3
<211> LENGTH: 20
<212> TYPE: DNA
<213> ORGANISM: artificial
<220> FEATURE:
<223> OTHER INFORMATION: primer CYC2f6

<400> SEQUENCE: 3
aagatcgaca cagctcacgg                                               20

<210> SEQ ID NO 4
<211> LENGTH: 20
<212> TYPE: DNA
<213> ORGANISM: artificial
<220> FEATURE:
<223> OTHER INFORMATION: primer CYC2r7

<400> SEQUENCE: 4
tctgcccttg actgattcac                                               20

<210> SEQ ID NO 5
<211> LENGTH: 330
<212> TYPE: DNA
<213> ORGANISM: artificial
<220> FEATURE:
<223> OTHER INFORMATION: PCR product of SEQ ID Nos. 3 and 4
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature

```
<222> LOCATION: (38)..(39)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t

<400> SEQUENCE: 5
tnngctgctn gtgccgggaa tanncgtgcn gggcgngnnt ntttcagggc agaagcattt    60
gctagggttt gacaaagtnt tgcaaaaccc ttgattggct ctttaccaag tccaagaccg   120
caattaagga gttggttgaa gaatgaaac acagttcatc ttctggtgct actgatcaat    180
gtgaggtttt tcaggagacc atcatgagga tatcaaatga aaagataaa ggcgaaaga    240 agaagtcagt acccaatgtt cttgaaggaa aaagaaaaa aactgcccga aaatataaat    300
ctggagtcga tgtgaatcag tcaagggcag                                   330

<210> SEQ ID NO 6
<211> LENGTH: 17
<212> TYPE: DNA
<213> ORGANISM: artificial
<220> FEATURE:
<223> OTHER INFORMATION: EcoRI adapter 1

<400> SEQUENCE: 6
ctcgtagact gcgtacc                                                  17

<210> SEQ ID NO 7
<211> LENGTH: 18
<212> TYPE: DNA
<213> ORGANISM: artificial
<220> FEATURE:
<223> OTHER INFORMATION: EcoRI adapter 2

<400> SEQUENCE: 7
aattggtacg cagtctac                                                 18

<210> SEQ ID NO 8
<211> LENGTH: 16
<212> TYPE: DNA
<213> ORGANISM: artificial
<220> FEATURE:
<223> OTHER INFORMATION: MseI adapter 1

<400> SEQUENCE: 8
gacgatgagt cctgag                                                   16

<210> SEQ ID NO 9
<211> LENGTH: 14
<212> TYPE: DNA
<213> ORGANISM: artificial
<220> FEATURE:
<223> OTHER INFORMATION: MseI adapter 2

<400> SEQUENCE: 9
tactcaggac tcat                                                     14

<210> SEQ ID NO 10
<211> LENGTH: 10
<212> TYPE: DNA
<213> ORGANISM: artificial
<220> FEATURE:
```

```
<223> OTHER INFORMATION: sequence with SNP
<220> FEATURE:
<221> NAME/KEY: misc_feature
<222> LOCATION: (6)..(6)
<223> OTHER INFORMATION: n is c, or t

<400> SEQUENCE: 10 tttganaaag                                                                    10

<210> SEQ ID NO 11
<211> LENGTH: 330
<212> TYPE: DNA
<213> ORGANISM: artificial
<220> FEATURE:
<223> OTHER INFORMATION: PCR product of SEQ ID Nos. 3 and 4 in normal
      flowering plants
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (16)..(18)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t

<400> SEQUENCE: 11
nnngcnngct cggtcnnncg gnntagncgt gcangggcgn gnntnttcaa gggcagaaga         60
tttgctaggg tttgataaag ctngcaaaac ccttgattgg ctctttacca agtccaagac        120
cgcaattaag gagttggttg aagaaatgaa acacagttca tcttctggtg ctactgatca        180
atgtgaggtt tttcaggaga ccatcatgag gatatcaaat gaaaaagata aaggcgaaaa        240
gaagaagtca gtacccaatg ttcttgaagg aaaaaagaaa aaaactgccc gaaaatataa        300
atctggagtc gatgtgaatc agtcaagggc                                        330
```